United States Patent
Niu et al.

(10) Patent No.: US 7,605,126 B2
(45) Date of Patent: Oct. 20, 2009

(54) ACYLAMINOHETEROARYL HEPATITIS C VIRUS PROTEASE INHIBITORS

(75) Inventors: Deqiang Niu, Lexington, MA (US); Joel D. Moore, Somerville, MA (US); Dong Liu, Waltham, MA (US); Yonghua Gai, North Grafton, MA (US); Zhigang Chen, Acton, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 185 days.

(21) Appl. No.: 11/503,502

(22) Filed: Aug. 11, 2006

(65) Prior Publication Data

US 2008/0039470 A1 Feb. 14, 2008

(51) Int. Cl.
- A61K 38/12 (2006.01)
- C07K 5/12 (2006.01)
- A61K 38/06 (2006.01)
- C07K 5/08 (2006.01)

(52) U.S. Cl. .......... 514/11; 514/18; 530/317; 530/331

(58) Field of Classification Search .......... None
See application file for complete search history.

(56) References Cited

U.S. PATENT DOCUMENTS

| 6,323,180 | B1 | 11/2001 | Linas-Brunet et al. | |
|---|---|---|---|---|
| 7,041,698 | B2 | 5/2006 | Ripka et al. | |
| 2005/0261200 | A1 | 11/2005 | Miao et al. | |
| 2007/0054842 | A1* | 3/2007 | Blatt et al. | 514/9 |
| 2007/0093414 | A1 | 4/2007 | Carini et al. | |
| 2007/0281884 | A1* | 12/2007 | Sun et al. | 514/10 |
| 2007/0281885 | A1* | 12/2007 | Sun et al. | 514/10 |
| 2008/0125444 | A1* | 5/2008 | Sun et al. | 514/255.05 |
| 2008/0181868 | A1* | 7/2008 | Sun et al. | 424/85.4 |

FOREIGN PATENT DOCUMENTS

WO    WO 2006/043145    4/2006

OTHER PUBLICATIONS

H.-K. Han. AAPS Pharmsci. (2000) 2(1), article 6, pp. 1-11.*
P. Ettmayer et al. J. Med. Chem. (2004) 47(10), pp. 2393-2404.*
B. Testa. Biochem. Pharm. (2004) 68, pp. 2097-2106.*
* cited by examiner Primary Examiner—Andrew D Kosar
(74) Attorney, Agent, or Firm—Carolyn S. Elmore; Edgar W. Harlan; Elmore Patent Law Group, P.C.

(57) ABSTRACT

The present invention discloses compounds of formulae I and II, or pharmaceutically acceptable salts, esters, or prodrugs thereof:

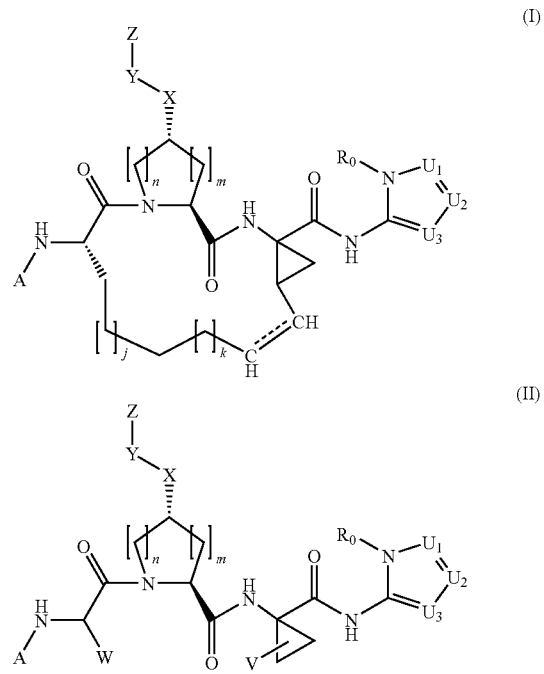

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

15 Claims, No Drawings

ACYLAMINOHETEROARYL HEPATITIS C VIRUS PROTEASE INHIBITORS

TECHNICAL FIELD

The present invention relates to novel hepatitis C virus (HCV) protease inhibitor compounds having antiviral activity against HCV and useful in the treatment of HCV infections. More particularly, the invention relates to novel acylaminoheteroaryl HCV protease inhibitor compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-.alpha. (IFN-a), while a new approved second-generation treatment involves co-treatment with IFN-a and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug must possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002). More relevant patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); US publications 20050153877, 20050261200 and 20050065073.

SUMMARY OF THE INVENTION

The present invention relates to novel HCV protease inhibitor compounds including pharmaceutically acceptable salts, esters, or prodrugs thereof which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

In one embodiment of the present invention there are disclosed compounds represented by Formulae I and II, or pharmaceutically acceptable salts, esters, or prodrugs thereof:

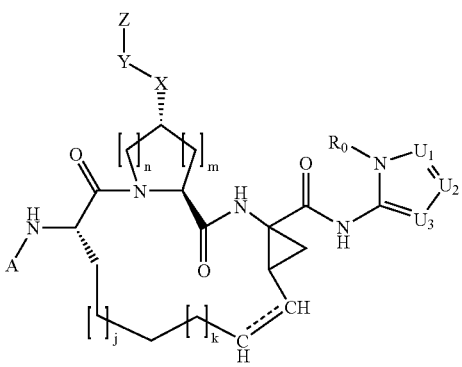

(I)

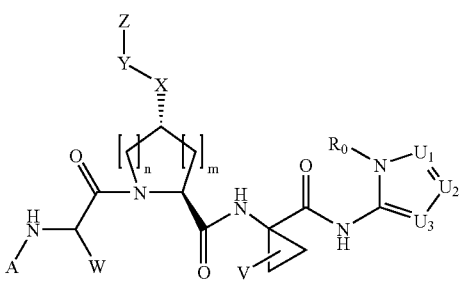

(II)

wherein
A is selected from H, —(C=O)—O—R₁, —(C=O)—R₂, —C(=O)—NH—R₂, or —S(O)₂—R₁, —S(O)₂NHR₂;
each R₁ is independently selected from the group consisting of:
(i) aryl;
(ii) substituted aryl;
(iii) heteroaryl;
(iv) substituted heteroaryl;
(v) heterocycloalkyl or substituted heterocycloalkyl;
(vi) —C₁-C₈ alkyl;
(vii) —C₂-C₈ alkenyl;
(viii) —C₂-C₈ alkynyl containing 0, 1, 2, or 3 heteroatoms selected from O, S, or N;
(ix) substituted —C₁-C₈ alkyl;
(x) substituted —C₂-C₈ alkenyl;
(xi) substituted —C₂-C₈ alkynyl containing 0, 1, 2, or 3 heteroatoms selected from O, S or N;
(xii) —C₃-C₁₂ cycloalkyl;
(xiii) substituted —C₃-C₁₂ cycloalkyl;
(xiv) —C₃-C₁₂ cycloalkenyl; and
(xv) substituted —C₃-C₁₂ cycloalkenyl;
each R₂ is independently selected from the group consisting of:
(i) hydrogen;
(ii) aryl;
(iii) substituted aryl;
(iv) heteroaryl;
(v) substituted heteroaryl;
(vi) heterocycloalkyl or;
(vii) substituted heterocycloalkyl;
(viii) —C₁-C₈ alkyl,
(ix) —C₂-C₈ alkenyl, or
(x) —C₂-C₈ alkynyl containing 0, 1, 2, or 3 heteroatoms selected from O, S, or N;
(xi) substituted —C₁-C₈ alkyl,
(xii) substituted —C₂-C₈ alkenyl, or
(xiii) substituted —C₂-C₈ alkynyl containing 0, 1, 2, or 3 heteroatoms selected from O, S or N;
(xiv) —C₃-C₁₂ cycloalkyl, or
(xv) substituted —C₃-C₁₂ cycloalkyl;
(xvi) —C₃-C₁₂ cycloalkenyl, or
(xvii) substituted —C₃-C₁₂ cycloalkenyl;
R₀ is H, Me, Et, —OH, or —C(O)NH₂.
U₁, U₂, and U₃ are independently selected from —CR₃ and N, wherein R₃ is independently selected from:
(i) hydrogen;
(ii) halogen;
(iii) —NO₂;
(iv) —CN;
(v) -M-R₄, Wherein M is absent, or O, S, NH, NR₅;
(vi) aryl; substituted aryl; heteroaryl; substituted heteroaryl;
(vii) heterocycloalkyl or substituted heterocycloalkyl;
Each R₄, R₅ is independently selected from:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —C₁-C₈ alkyl;
(ix) —C₂-C₈ alkenyl;
(x) —C₂-C₈ alkynyl containing 0, 1, 2, or 3 heteroatoms selected from O, S, or N;
(xi) substituted —C₁-C₈ alkyl;
(xii) substituted —C₂-C₈ alkenyl;
(xiii) substituted —C₂-C₈ alkynyl containing 0, 1, 2, or 3 heteroatoms selected from O, S or N;
(xiv) —C₃-C₁₂ cycloalkyl;
(xv) substituted —C₃-C₁₂ cycloalkyl;
(xvi) —C₃-C₁₂ cycloalkenyl; and
(xvii) substituted —C₃-C₁₂ cycloalkenyl;
L is selected from —CH₂—, —O—, —S—, —S(O)₂—, —CO—, —C(O)O—, —C(O)NH—, —CHF—, —CF₂—, aryl, substituted aryl, heteroaryl, substituted heteroaryl;
W and V are independently selected from the group consisting of:
(i) hydrogen;
(ii) aryl;
(iii) substituted aryl;
(iv) heteroaryl;
(v) substituted heteroaryl;
(vi) heterocyclic or;
(vii) substituted heterocyclic;
(viii) —C₁-C₈ alkyl;
(ix) —C₂-C₈ alkenyl;
(x) —C₂-C₈ alkynyl;
(xi) substituted —C₁-C₈ alkyl;
(xii) substituted —C₂-C₈ alkenyl;
(xiii) substituted —C₂-C₈ alkynyl containing 0, 1, 2, or 3 heteroatoms selected from O, S or N;
(xiv) —C₃-C₁₂ cycloalkyl;
(xv) substituted —C₃-C₁₂ cycloalkyl;
(xvi) —C₃-C₁₂ cycloalkenyl; and
(xvii) substituted —C₃-C₁₂ cycloalkenyl;
X is absent or is selected from the group consisting of:
(i) oxygen;
(ii) sulfur; and
(iii) NR₄; where R₄ is as previously defined above;
Y is absent or is selected from the group consisting of:
(i) —C₁-C₆ alkyl containing 0, 1, 2, or 3 heteroatoms selected from O, S, or N, optionally substituted with one or more substituent selected from halogen, aryl, substituted aryl, heteroaryl, or substituted heteroaryl;

(ii) —$C_2$-$C_6$ alkenyl containing 0, 1, 2, or 3 heteroatoms selected from O, S, or N, optionally substituted with one or more substituent selected from halogen, aryl, substituted aryl, heteroaryl, or substituted heteroaryl;

(iii) —$C_2$-$C_6$ alkynyl containing 0, 1, 2, or 3 heteroatoms selected from O, S, or N, optionally substituted with one or more substituent selected from halogen, aryl, substituted aryl, heteroaryl, or substituted heteroaryl;

(iv) —$C_3$-$C_{12}$ cycloalkyl;

(v) substituted —$C_3$-$C_{12}$ cycloalkyl;

(vi) heterocycloalkyl; and (vii) substituted heterocycloalkyl;

Z is selected from aryl, substituted aryl, heteroaryl, and substituted heteroaryl;

j=0, 1, 2, 3, or 4;

k=1, 2, or 3;

m=0, 1, or 2;

n=1, or 2; and

----- denotes a carbon-carbon single or double bond.

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

A second embodiment of the invention is a compound represented by Formula II as described herein, or a pharmaceutically acceptable salt, ester or prodrug thereof, alone or in combination with a pharmaceutically acceptable carrier or excipient.

Certain aspects of the invention include, but are not limited to:

A compound of Formulae III and IV:

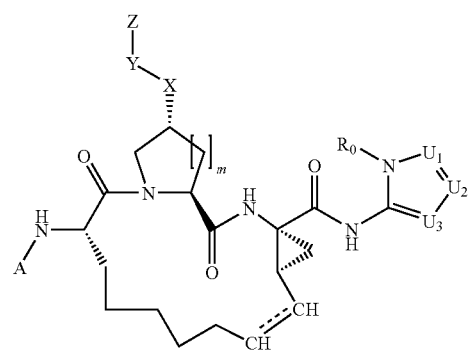

(III)

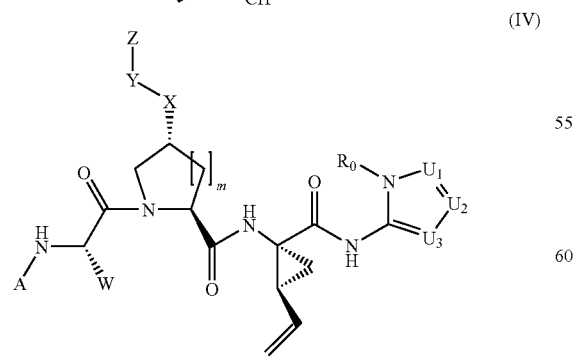

(IV)

where A, X, Y, Z, W, $R_0$, $U_1$, $U_2$ and $U_3$ are as defined in Formula I.

A compound of Formulae V and VI:

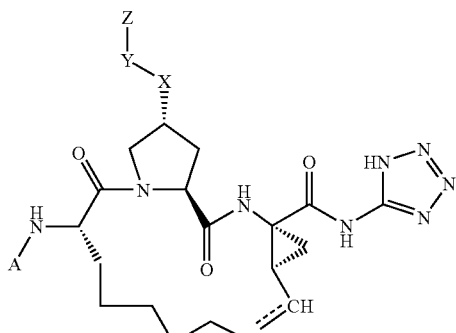

(V)

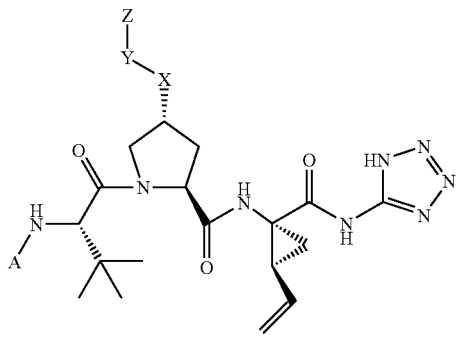

(VI)

where A, X, Y, and Z are as defined in Formula I.

A compound of Formulae VII and VIII:

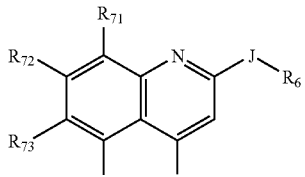

(VII)

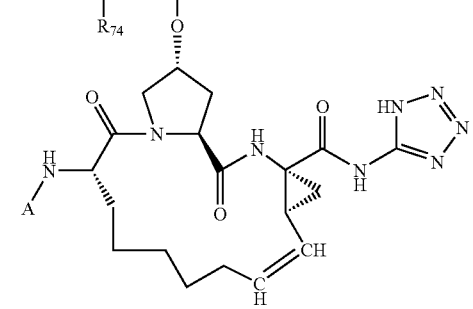

(VIII)

wherein R$_6$ is selected from aryl, substituted aryl, heteroaryl, and substituted heteroaryl; J is absent, O, S, NR$_5$, CO, (CO)NR$_5$, (CO)O, NR$_5$(CO), NH(CO)NH, NR$_5$SO$_2$; wherein A and R$_5$ are as defined in Formula I;

each R$_{71}$, R$_{72}$, R$_{73}$ and R$_{74}$ is absent or independently selected from:
(i) hydrogen;
(ii) halogen;
(iii) —NO$_2$;
(iv) —CN;
(v) —M-R$_4$, wherein M is absent, or O, S, NH, NR$_5$;
(vi) aryl;
(vii) substituted aryl;
(viii) heteroaryl;
(ix) substituted heteroaryl;
(x) heterocycloalkyl; and
(xi) substituted heterocycloalkyl;
wherein R$_4$, R$_5$ are as defined previously in Formula I.

A compound of Formulae IX and X:

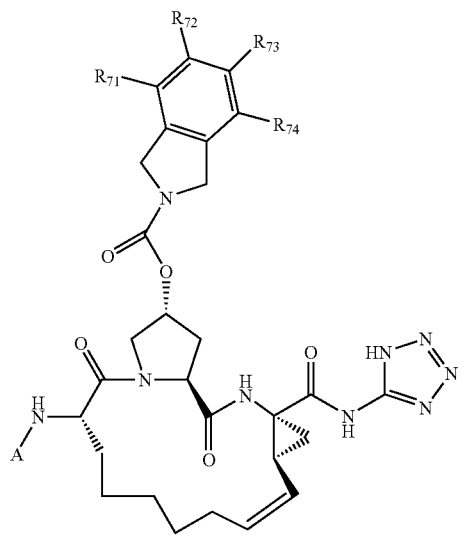

(IX)

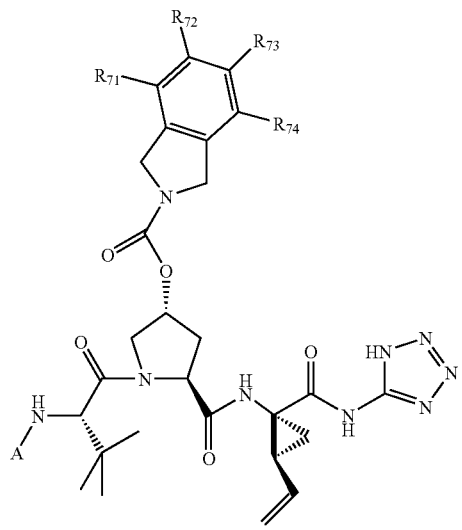

(X)

wherein each R$_{71}$, R$_{72}$, R$_{73}$, and R$_{74}$ are as defined previously in Formulae VII and VIII; and A is as defined in Formula I.

A compound of Formulae XI and XII:

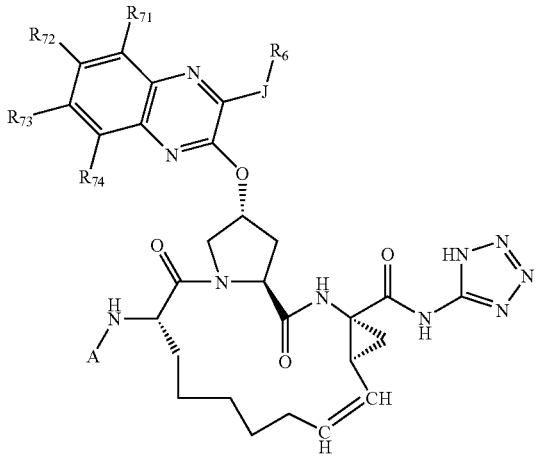

(XI)

(XII)

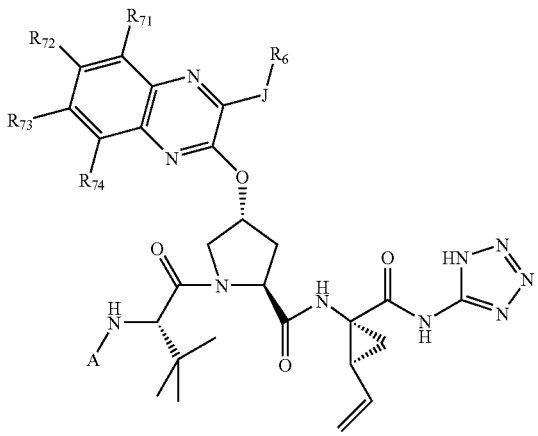

wherein each R$_6$, R$_{71}$, R$_{72}$, R$_{73}$, R$_{74}$ and J are as defined previously in Formulae VII and VIII; and A is as defined in Formula I.

A compound of Formulae XIII and XIV:

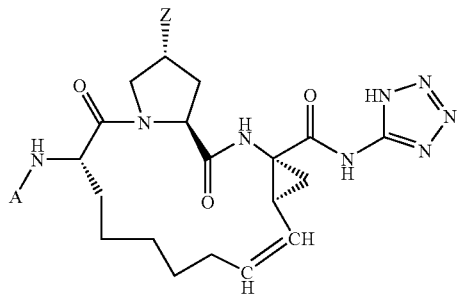

(XIII)

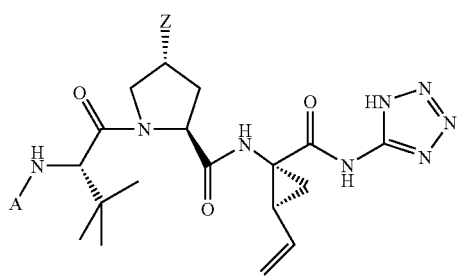

(XIV)

wherein A and Z are as defined previously in Formula I.

Representative compounds of the invention include, but are not limited to, compounds 2-25 of the Formula XV:

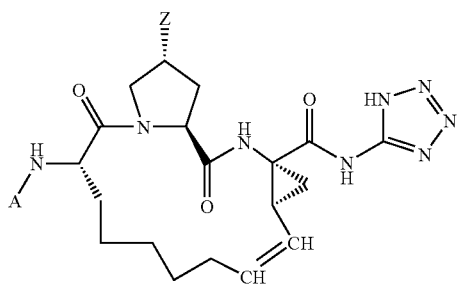
(XIII)

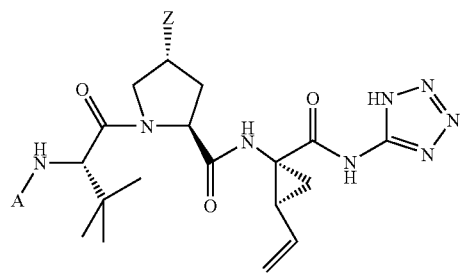
(XIV)

wherein A, Q and G are delineated for each example in Table 1

TABLE 1

| Example# | A | Q | G |
|---|---|---|---|
| 2 | cyclopentyl-OC(O)-CH(CH3)- | 3-(thiophen-2-yl)-2-(isopropoxy)quinoxalinyl | isopropyl-NH-tetrazole |
| 3 | cyclopentyl-OC(O)-CH(CH3)- | 7-methoxy-4-(isopropoxy)-2-[2-(isopropylamino)thiazol-4-yl]quinolinyl | isopropyl-NH-tetrazole |
| 4 | tert-butyl-OC(O)-CH(CH3)- | 3-(thiophen-2-yl)-2-(isopropoxy)quinoxalinyl | isopropyl-NH-tetrazole |
| 5 | cyclopentyl-OC(O)-CH(CH3)- | 3-(thiophen-2-yl)-2-(isopropoxy)quinoxalinyl | isopropyl-NH-(1-methyl)tetrazole |

TABLE 1-continued

| Example# | A | Q | G |
|---|---|---|---|
| 6 | | | |
| 7 | | | |
| 8 | | | |
| 9 | | | |
| 10 | | | |
| 11 | | | |
| 12 | | | |

TABLE 1-continued

| Example# | A | Q | G |
|---|---|---|---|
| 13 | cyclobutyl 2-methylpropanoate ester | 2-(thiophen-2-yl)-3-ethoxyquinoxaline | N-isopropyl-1H-tetrazol-5-amine |
| 14 | tert-butyl 2-methylpropanoate ester | 2-styryl-3-ethoxyquinoxaline | N-isopropyl-1H-tetrazol-5-amine |
| 15 | tert-butyl 2-methylpropanoate ester | 2-(2-(thiophen-3-yl)vinyl)-3-ethoxyquinoxaline | N-isopropyl-1H-tetrazol-5-amine |
| 16 | tert-butyl 2-methylpropanoate ester | 2-(2-(thiazol-2-yl)ethyl)-3-ethoxyquinoxaline | N-isopropyl-1H-tetrazol-5-amine |
| 17 | cyclopentyl 2-methylpropanoate ester | 5,8-dimethoxy-2-(thiophen-2-yl)-3-ethoxyquinoxaline | N-isopropyl-1H-tetrazol-5-amine |
| 18 | cyclopentyl 2-methylpropanoate ester | 6,7-dichloro-2-(thiophen-2-yl)-3-ethoxyquinoxaline | N-isopropyl-1H-tetrazol-5-amine |
| 19 | cyclopentyl 2-methylpropanoate ester | 6-methoxy-2-(thiophen-2-yl)-3-ethoxyquinoxaline | N-isopropyl-1H-tetrazol-5-amine |

TABLE 1-continued
| Example# | A | Q | G |
|---|---|---|---|
| 20 | 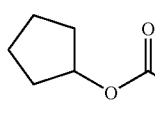 | 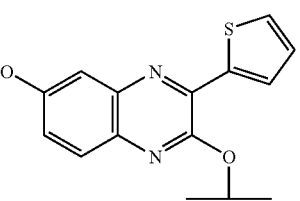 | 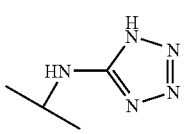 |
| 21 | 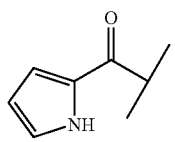 | 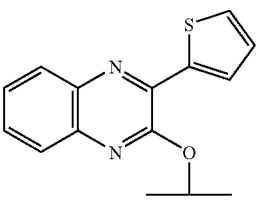 | 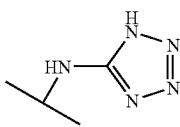 |
| 22 | 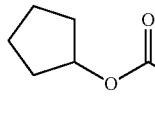 | 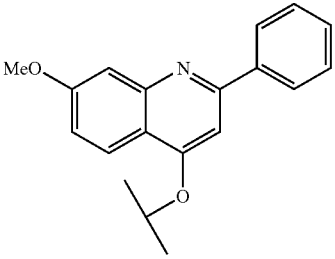 | 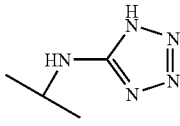 |
| 23 | 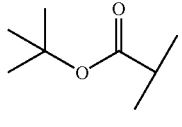 | 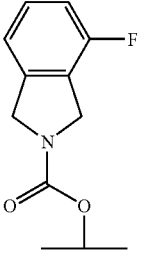 | 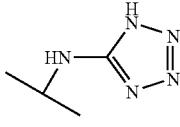 |
| 24 | 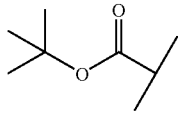 | 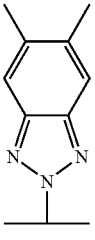 | 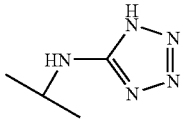 |
| 25 | 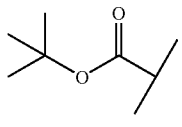 | 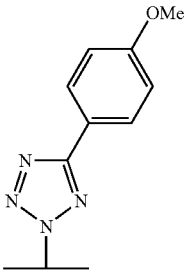 | 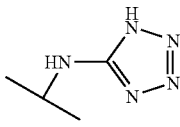 |

Representative compounds of the invention include, but are not limited to, the compounds 26-49 of the Formula XVI:
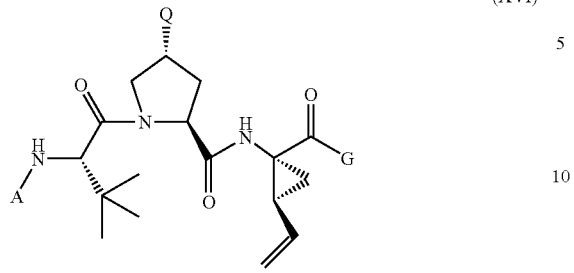
(XVI)
wherein A, Q and G are delineated for each example in Table 2:
TABLE 2
| Example# | A | Q | G |
|---|---|---|---|
| 26 | | | |
| 27 | | | |
| 28 | | | |
| 29 | | | |

TABLE 2-continued

| Example# | A | Q | G |
|---|---|---|---|
| 30 | | | |
| 31 | | | |
| 32 | | | |
| 33 | | | |
| 34 | | | |
| 35 | | | |
| 36 | | | |

TABLE 2-continued

| Example# | A | Q | G |
|---|---|---|---|
| 37 | | | |
| 38 | | | |
| 39 | | | |
| 40 | | | |
| 41 | | | |
| 42 | | | |
| 43 | | | |

TABLE 2-continued
| Example# | A | Q | G |
|---|---|---|---|
| 44 | 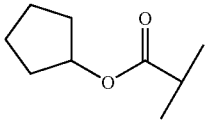 | 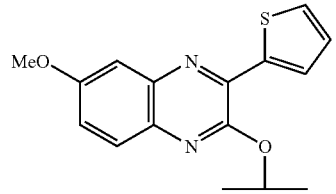 | 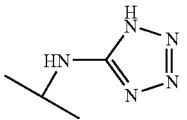 |
| 45 | 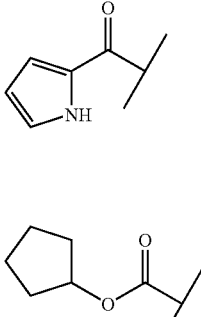 | 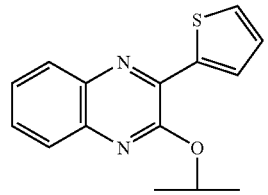 | 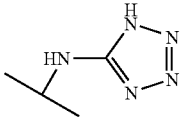 |
| 46 | 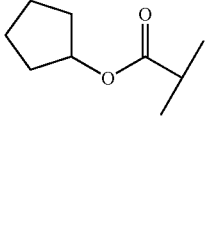 | 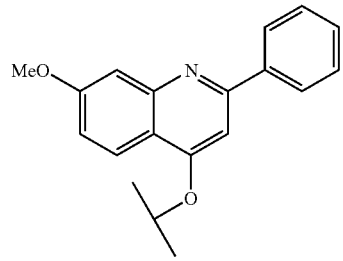 | 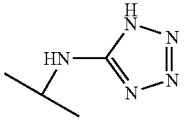 |
| 47 | 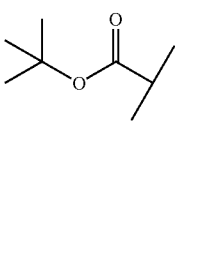 | 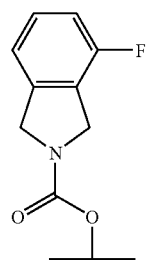 | 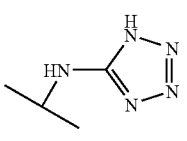 |
| 48 | 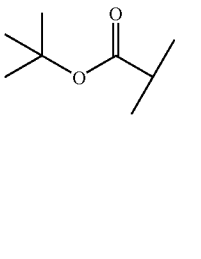 | 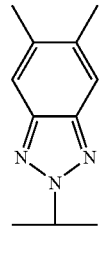 | 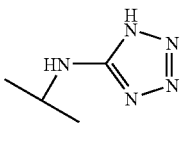 |
| 49 | 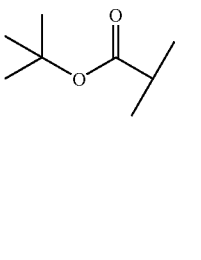 | 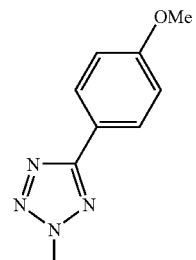 | 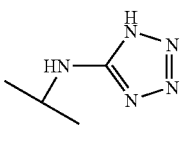 |

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

In another embodiment, the pharmaceutical compositions of the present invention may further contain other anti-HCV agents. Examples of anti-HCV agents include, but are not limited to, .alpha.-interferon, .beta.-interferon, ribavirin, and amantadine.

In another embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to a another embodiment, the present invention includes methods of treating hepatitis C infections in a subject in need of such treatment by administering to said subject an therapeutically effective amount of the pharmaceutical compounds or compositions of the present invention. The methods can further include administration of an additional therapeutic agent, including another antiviral agent or an anti-HCV agent. The additional agent can be co-administered, concurrently administered or sequentially administered with the compound or composition delineated herein. The methods herein can further include the step of identifying that the subject is in need of treatment for hepatitis C infection. The identification can be by subjective (e.g., health care provider determination) or objective (e.g., diagnostic test) means.

Definitions

Listed below are definitions of various terms used to describe this invention. These definitions apply to the terms as they are used throughout this specification and claims, unless otherwise limited in specific instances, either individually or as part of a larger group.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a monovalent group derived from a hydrocarbon moiety containing from two to six, or two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety containing from two to six, or two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom, respectively. Examples of $C_3$-$C_8$-cycloalkyl include, but not limited to, cyclopropyl, cyclobutyl, cyclopentyl, cyclohexyl, cycloheptyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted", "substituted $C_1$-$C_6$ alkyl," "substituted $C_1$-$C_8$ alkyl," "substituted $C_2$-$C_6$ alkenyl," "substituted $C_2$-$C_8$ alkenyl," "substituted $C_2$-$C_6$ alkynyl", "substituted $C_2$-$C_8$ alkynyl", "substituted $C_3$-$C_{12}$ cycloalkyl," "substituted $C_3$-$C_8$ cycloalkenyl," "substituted $C_3$-$C_{12}$ cycloalkenyl," "substituted aryl", "substituted heteroaryl," "substituted arylalkyl", "substituted heteroarylalkyl," "substituted heterocycloalkyl," as used herein, refer to CH, NH, $C_1$-$C_6$ alkyl, $C_1$-$C_8$ alkyl, $C_2$-$C_6$ alkenyl, $C_2$-$C_8$ alkenyl, $C_2$-$C_6$ alkynyl, $C_2$-$C_8$ alkynyl, $C_3$-$C_{12}$ cycloalkyl, $C_3$-$C_8$ cycloalkenyl, $C_3$-$C_{12}$ cycloalkenyl, aryl, heteroaryl, arylalkyl, heteroarylalkyl, heterocycloalkyl groups as previously defined, substituted by independent replacement of one, two, or three or more of the hydrogen atoms thereon with substituents including, but not limited to, —F, —Cl, —Br, —I, —OH, protected hydroxy, —$NO_2$, —CN, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention that the substituted or unsubstituted alkyl, alkenyl, alkynyl, cycloalkyl, cycloalkenyl, cycloalkynyl, arylalkyl, heteroarylalkyl, and heterocycloalkyl are intended to be divalent or trivalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a nontoxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil;

safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

An additional method of the present invention is the treatment of biological samples with an inhibitory amount of a compound of the present invention in such amounts and for such time as is necessary to inhibit viral replication and/or reduce viral load in the biological sample. The term "inhibitory amount" means a sufficient amount to inhibit viral replication and/or decrease the hepatitis C viral load in a biological sample. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof; or stem cells. Thus another embodiment of the present invention is a method of treating a biological sample by contacting said biological sample with an inhibitory amount of a compound or pharmaceutical composition of the present invention.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DUPHOS for

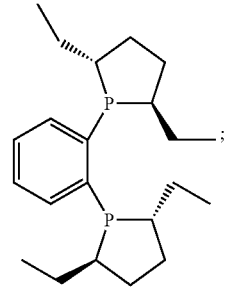

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for O-(7-Azabenzotriazole-1-yl)-N,N,N',N'-tetramethyluronium hexafluorophosphate;
Hoveyda's Cat. for Dichloro(o-isopropoxyphenylmethylene)(tricyclohexylphosphine)ruthenium(II);
KHMDS is potassium bis(trimethylsilyl)amide;
Ms for mesyl;
NMM for N-4-methylmorpholine
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran;
TLC for thin layer chromatography;
TPP or PPh$_3$ for triphenylphosphine;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared.

Scheme 1.

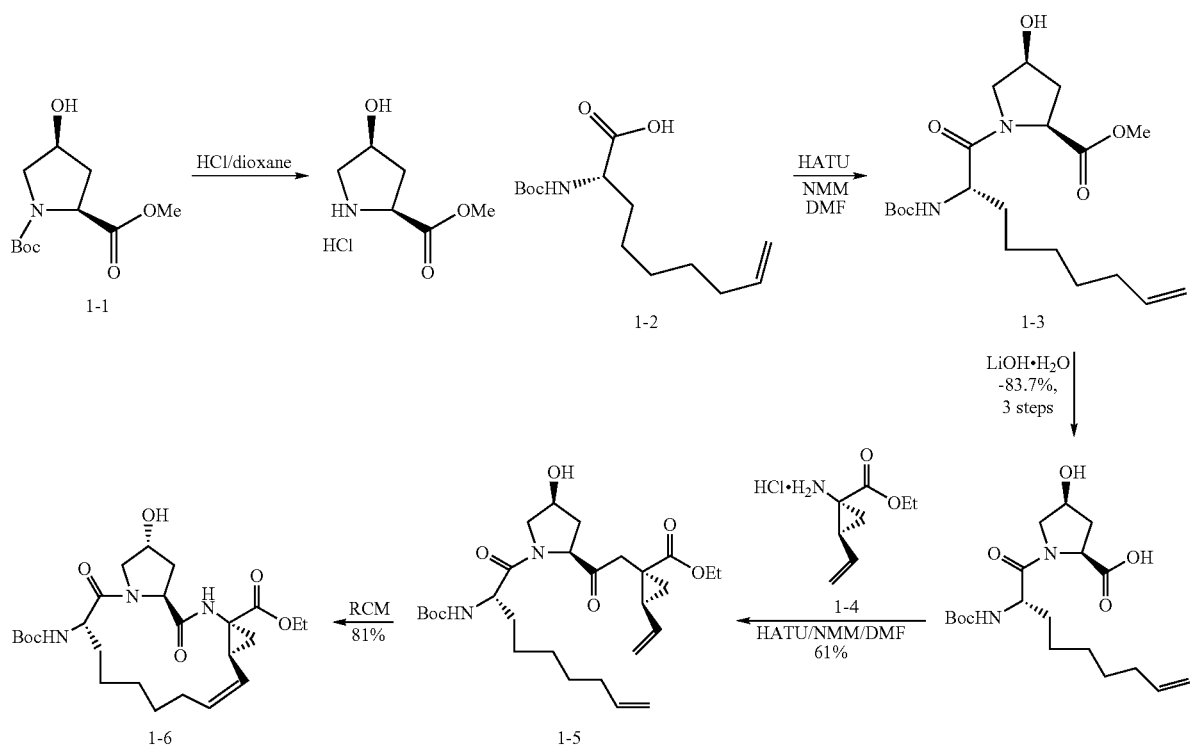

All of the quinoxaline analogs were prepared from the common intermediate 1-6. The synthesis of compound 1-6 is outlined in Scheme 1. Deprotection of commercially available Boc-hydroxyproline 1-1 with HCl in dioxane followed by coupling with acid 1-2 using HATU, afforded intermediate 1-3. Other amino acid derivatives containing a terminal alkene may be used in place of 1-2 in order to generate varied macrocyclic structures (for further details see WO/0059929). Hydrolysis of 1-3 with LiOH followed by subsequent peptide coupling with cyclopropyl-containing amine 1-4 yielded tripeptide 1-5. Finally, ring-closing metathesis with a ruthenium-based catalyst gave the desired key intermediate 1-6 (for further details on ring closing metathesis see recent reviews: Grubbs et al., *Acc. Chem. Res.*, 1995, 28, 446; Shrock et al., *Tetrahedron* 1999, 55, 8141; Furstner, A. *Angew. Chem. Int. Ed.* 2000, 39, 3012; Trnka et al., *Acc. Chem. Res.* 2001, 34, 18; and Hoveyda et al., *Chem. Eur. J.* 2001, 7, 945).

Scheme 2.

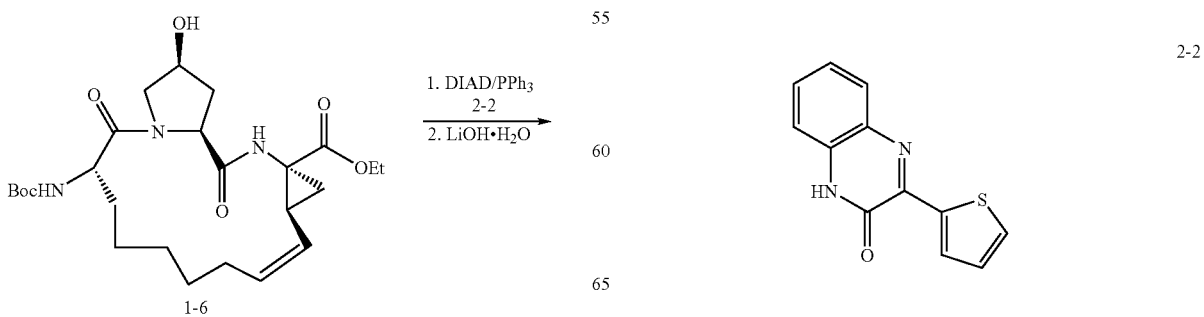

-continued

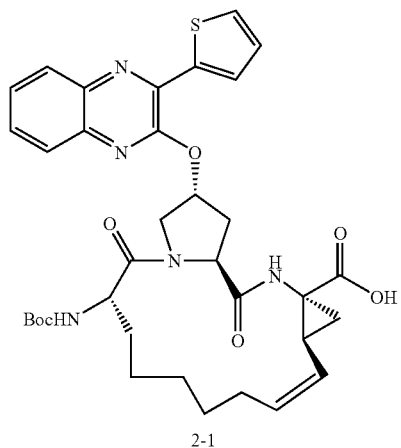

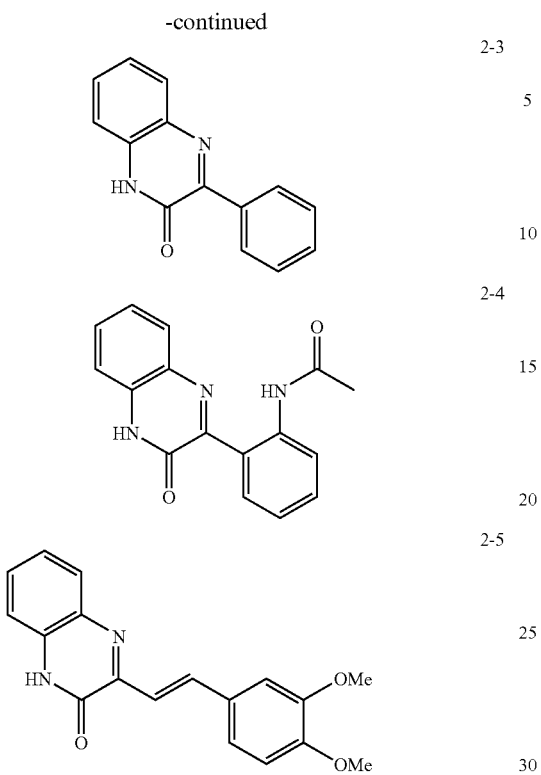

The quinoxaline analogs of the present invention were prepared via several different synthetic routes. The simplest method, shown in Scheme 2, was to condense commercially available 1H-quinoxalin-2-one analogs including, but not limited to, compounds 2-2-2-5 with key intermediate 1-6 by using Mitsunobu conditions followed by hydrolysis with LiOH. The existing literature predicts Mistonobu product formation at the 1 position nitrogen, however attachment at the carbonyl oxygen was observed to form compound 2-1. A detailed discussion of the identification and characterization of the unexpected oxo Mitosunobu addition product appears in the examples herein. For further details on the Mitsunobu reaction, see O. Mitsunobu, *Synthesis* 1981, 1-28; D. L. Hughes, *Org. React.* 29, 1-162 (1983); D. L. Hughes, *Organic Preparations and Procedures Int.* 28, 127-164 (1996); and J. A. Dodge, S. A. Jones, *Recent Res. Dev. Org. Chem.* 1, 273-283 (1997).

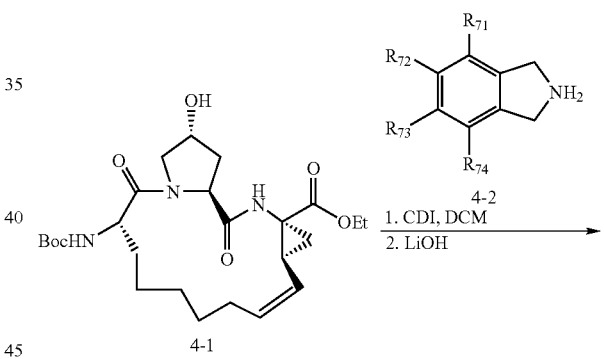

The quinoline analogs 3-1 of the present invention were prepared via a regular Mitsunobu reaction between the commercially available or otherwise easily synthesized quinolines 3-2 and the macrocyclic 1-6 followed by hydrolysis with LiOH (Scheme 3).

Scheme 4.

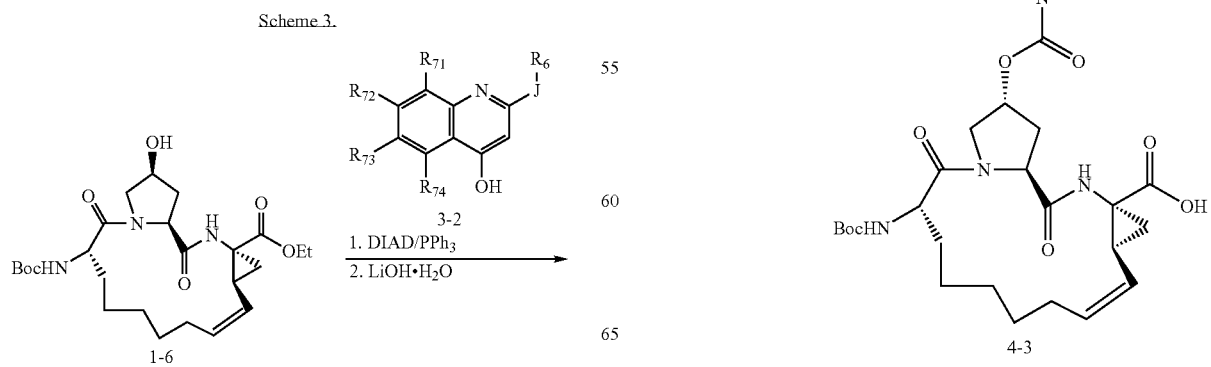

The macrocyclic starting material 4-1 was prepared following Scheme-1 by starting with the commercially available trans-Boc-hydroxyproline. Compounds of Formula 4-3 (the carbamates) were prepared by reacting 4-1 with CDI and isoindoline derivatives 4-2 followed by hydrolysis with LiOH (Scheme 4). R71, R72, R73 and R74 are as previously defined in Formula I.

The tetrazole or triazole analogs of the present invention (5-2 and 5-3) are prepared by one of the two methods. 1) Through the cyclic precursor mesylate 5-1: 5-1 was synthesized by forming the mesylate upon the hydroxyl of the hydroxyl proline residue of the cyclic peptide precursor 1-6 via the synthetic route generally described above in Scheme 5. The compounds of the present invention are made via the replace-

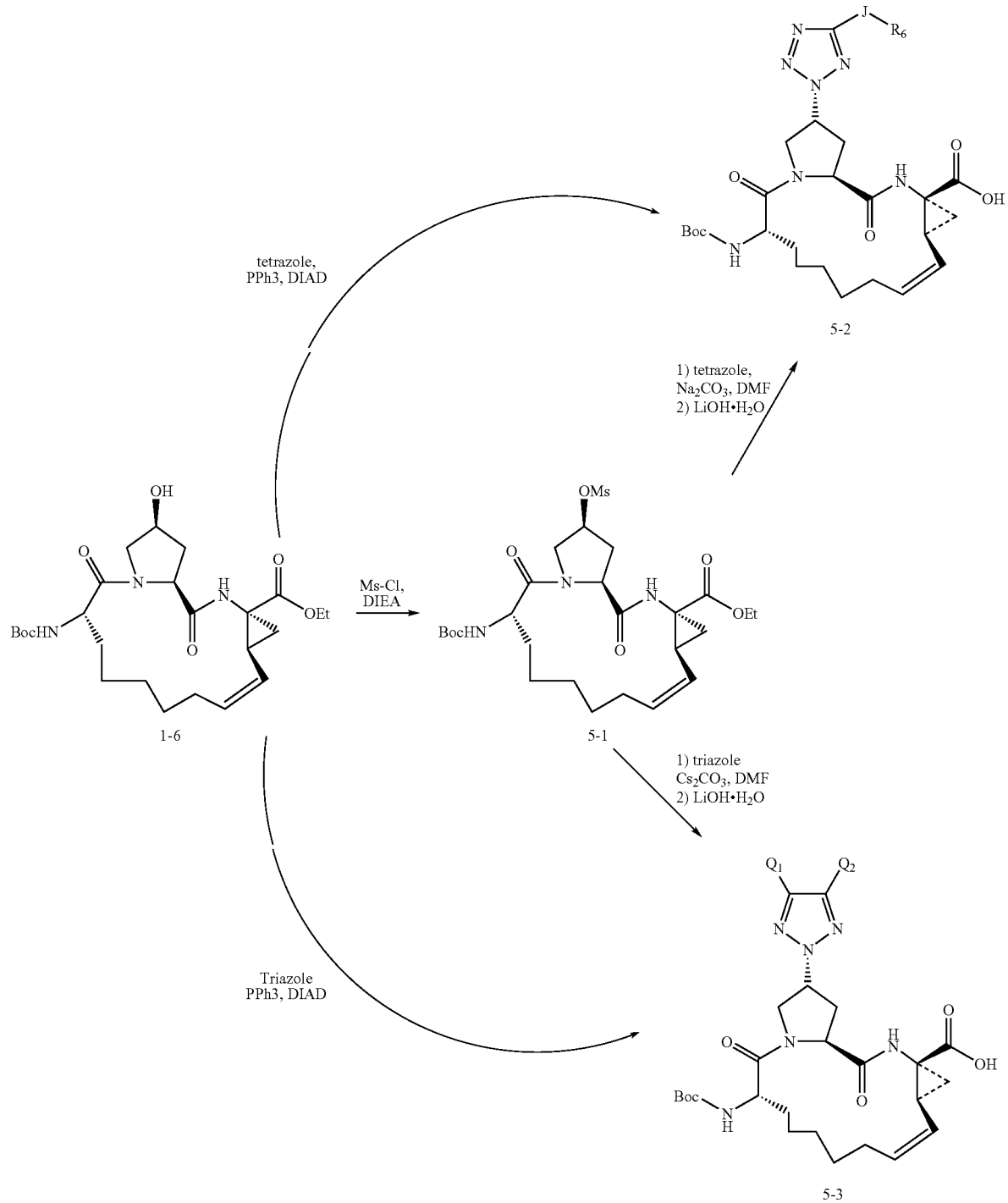

ment of the mesylate of the macrocyclic peptide mesylate 5-1 with a 5-substituted-2H-tetrazole, or a 4,5-substituted-1H-triazole, wherein Q1, Q2 is independently selected from -J-R6, and -J-R6 is as previously defined. 2) Through a Mitsunobu reaction between the compound 1-6 and a 5-substituted-2H-tetrazole, or a 4,5-substituted-1H-triazole, wherein Q1, Q2 is independently selected from -J-R6, and -J-R6 is as previously defined. Exemplary syntheses of such tetrazoloes and triazoles and further details of the mesylate replacement method could be found in the commonly assigned patent applications U.S. Ser. No. 10/360,947 (filed Feb. 7, 2003) and Ser. No. 10/365,854 (filed Feb. 13, 2003).

Scheme 6.

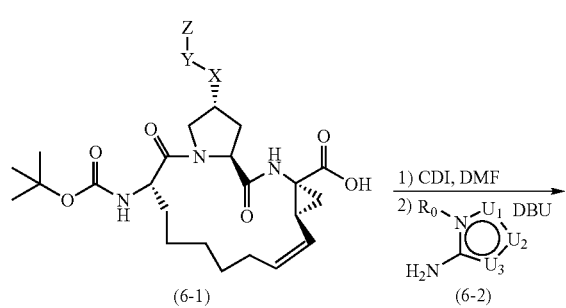

(6-1)    (6-2)

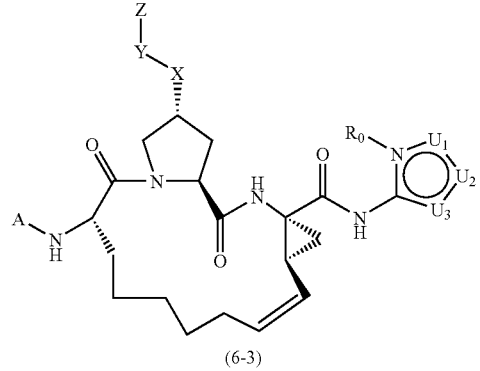

(6-3)

Scheme 6 illustrates the modification of the C-terminal of the macrocycle. The compounds 6-3 could be prepared by the reaction sequence of: 1) activation of the acid moiety of compound 6-1 by using a commonly known condensing reagent (i.e. CDI, HATU, EDC and the like); 2) followed by treatment with appropriate heteroaryl amines or substituted heteroaryl amines 6-2 including, but not limited to aminotetrazole, aminotriazole groups. Wherein A, X, Y, Z, R0, U1, U2 and U3 are as previously defined in Formula I.

Scheme 7.

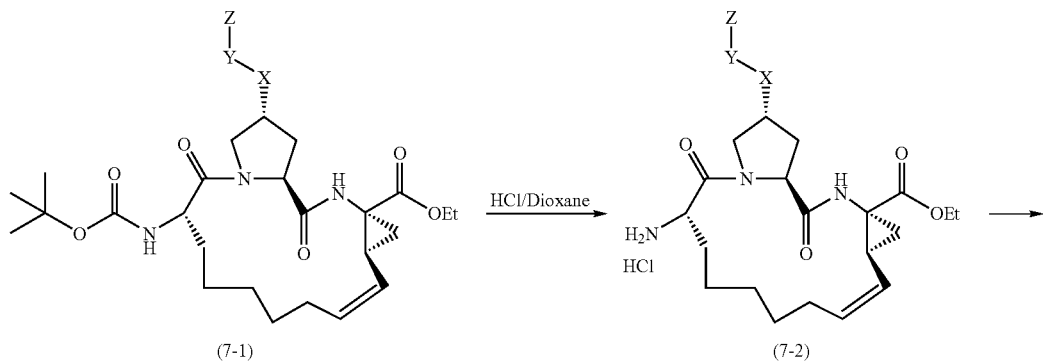

(7-1)    (7-2)

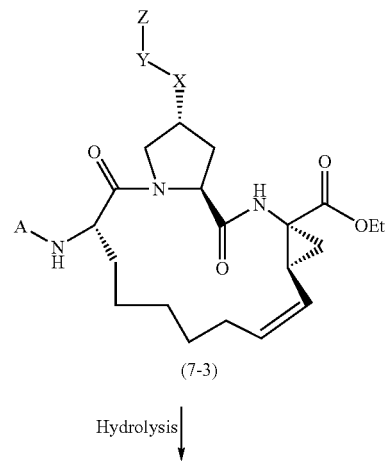

(7-3)

Hydrolysis

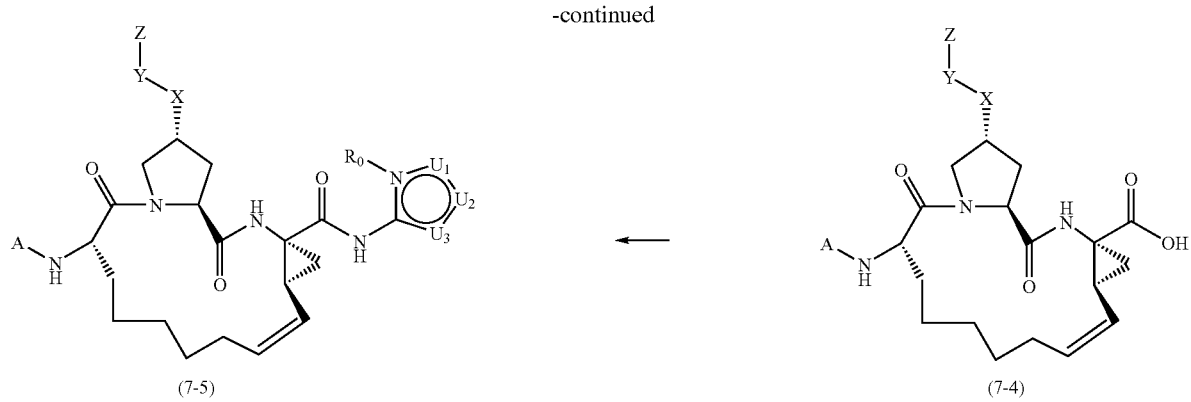

(7-5)    (7-4)

Scheme 7 illustrates the modification of the N-terminal and C-terminal of the macrocycle. Deprotection of the boc moiety with an acid, such as, but not limited to hydrochloric acid yields compounds of formula (7-2). The amino moiety of formula (7-2) can be alkylated or acylated with appropriate alkyl halide or acyl groups to give compounds of formula (7-3). Compounds of formula (7-3) can be hydrolyzed with base such as lithium hydroxide to free up the acid moiety of formula (7-4). Subsequent activation of the acid moiety (i.e. CDI, HATU, EDC and the like) followed by treatment with appropriate heteroaryl amines or substituted heteroaryl amines including, but not limited to aminotetrazole, aminotriazole groups to provide compounds of formula (7-5), wherein A, X, Y, Z, R0, U1, U2 and U3 are as previously defined in Formula I.

Scheme 8.

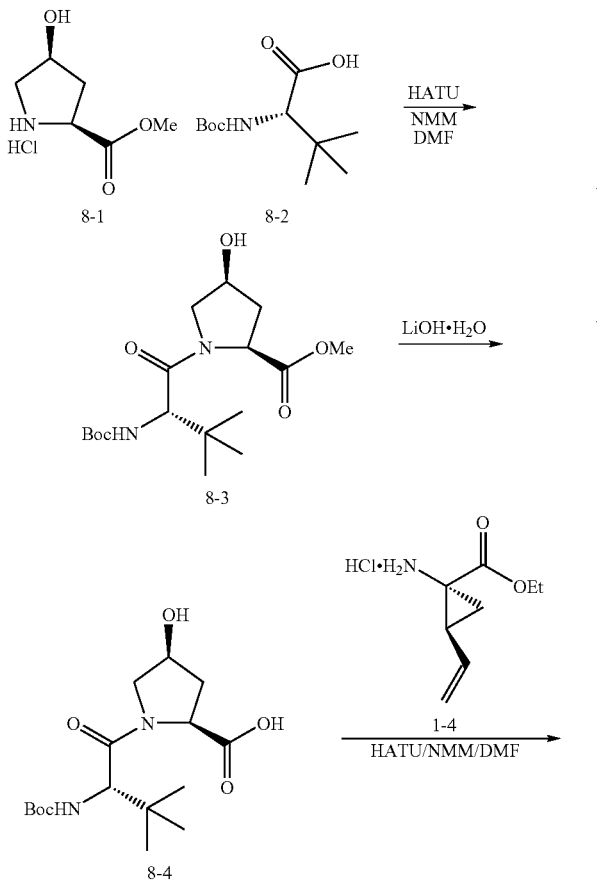

Scheme 8 outlines the general route for the preparation of acyclic derivatives of the compounds with the structure 8-6. The synthesis of compound 8-5 is analog to the synthesis of compound 1-5 shown in Scheme 1. Coupling of the commercially available compound 8-1 with acid 8-2 using HATU, afforded intermediate 8-3. Hydrolysis of 8-3 with LiOH followed by subsequent peptide coupling with cyclopropyl-containing amine 1-4 yielded tri-peptide 8-5. Compound 8-5 was converted to compound 8-6 by the methods described in Schemes 2-7 by using the acyclic starting material in the place of the macrocyclic cores.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims

Example 1

Synthesis of the Cyclic Peptide Precursor organic phase was dried over anhydrous $Na_2SO_4$, filtered, and then concentrated in vacuo. The residue was purified by silica gel flash chromatography using gradient elution with hexanes:EtOAc (5:1→3:1→1:1→1:2→1:5). The linear tripeptide 1f was isolated as an oil (1.59 g, 65.4%) and identified by HPLC (Retention time=11.43 min) and MS (found 544.84, M+Na$^+$).

1D. Ring Closing Metathesis (RCM). A solution of the linear tripeptide 1f (1.51 g, 2.89 mmol) in 200 ml dry DCM

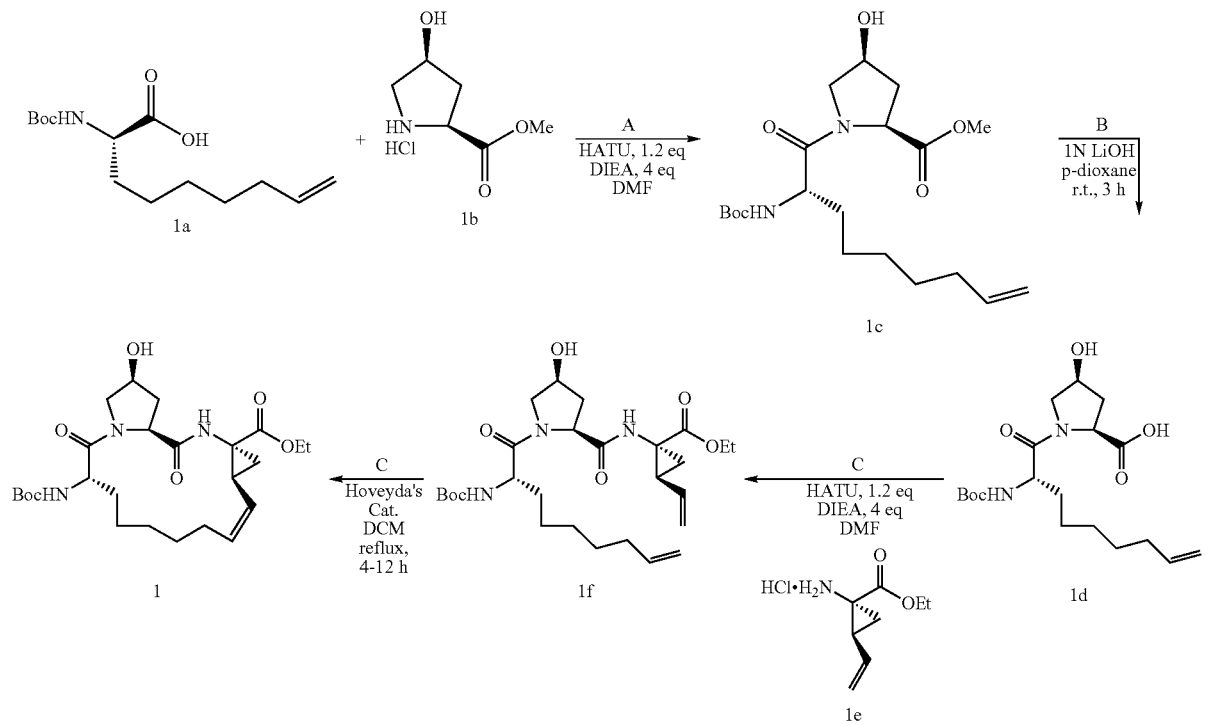

1A. To a solution of Boc-L-2-amino-8-nonenoic acid 1a (1.36 g, 5 mol) and the commercially available cis-L-hydroxyproline methyl ester 1b (1.09 g, 6 mmol) in 15 ml DMF, DIEA (4 ml, 4 eq.) and HATU (4 g, 2 eq) were added. The coupling was carried out at 0° C. over a period of 1 hour. The reaction mixture was diluted with 100 mL EtOAc, and directly washed with 5% citric acid (2×20 ml), water (2×20 ml), 1M $NaHCO_3$ (4×20 ml) and brine (2×10 ml). The organic phase was dried over anhydrous $Na_2SO_4$, filtered, and then concentrated in vacuo, affording the dipeptide 1c (1.91 g, 95.8%) that was identified by HPLC (Retention time=8.9 min, 30-70%, 90% B), and MS (found 421.37, M+Na$^+$).

1B. Dipeptide 1c (1.91 g) was dissolved in 15 mL of dioxane and 15 mL of 1 N LiOH aqueous solution, and the resulting mixture was stirred at room temperature for 4 hours. The reaction mixture was acidified by 5% citric acid and extracted with 100 mL EtOAc. The organic portion was then washed with water (2×20 ml), 1M $NaHCO_3$ (2×20 ml) and brine (2×20 ml). The organic phase was dried over anhydrous $Na_2SO_4$, filtered, and then concentrated in vacuo, yielding the free carboxylic acid compound 1d (1.79 g, 97%), which was used directly without the need for further purification 1C. To a solution of the free acid obtained above (1.77, 4.64 mmol) in 5 ml DMF, D-β-vinyl cyclopropane amino acid ethyl ester 1e (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and washed with 5% citric acid (2×20 ml), water (2×20 ml), 1M $NaHCO_3$ (4×20 ml), and brine (2×10 ml). The was deoxygenated by $N_2$ bubbling. Hoveyda's 1$^{st}$ generation catalyst (5 mol % eq.) was then added as a solid. The reaction was refluxed under $N_2$ atmosphere for 12 hours. The solvent was evaporated and the residue was purified by silica gel flash chromatography using gradient elution with hexanes:EtOAc (9:1→5:1→3:1→1:1→1:2→1:5). The cyclic peptide precursor 1 was isolated as a white powder (1.24 g, 87%), and identified by HPLC (Retention time=7.84 min, 30-70%, 90% B), and MS (found 516.28, M+Na$^+$). For further details of the synthetic methods employed to produce the cyclic peptide precursor 1, see WO 00/059929 (2000).

Example 2

Compound of Formula XV, wherein

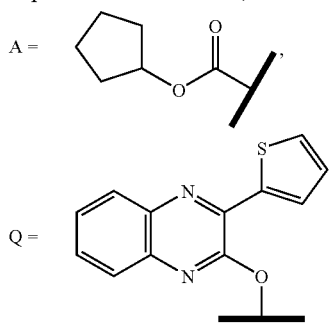

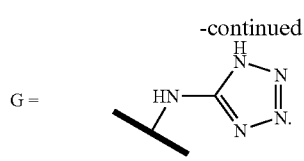

Step 2A.

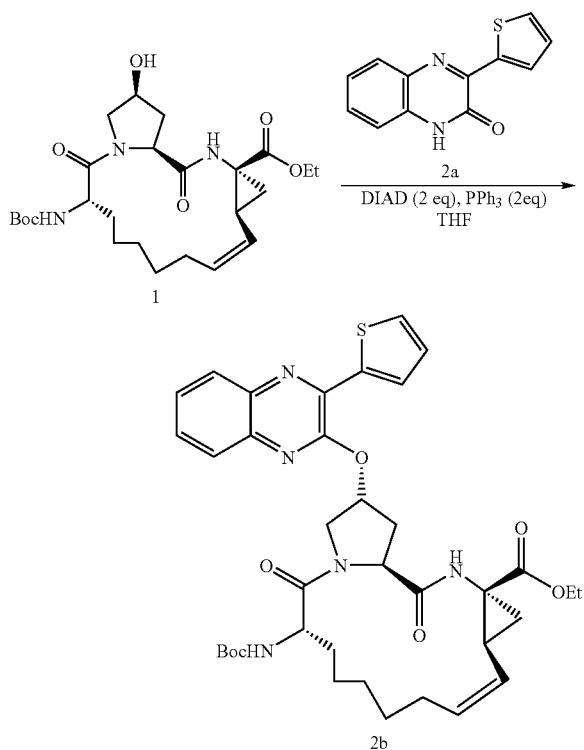

To a cooled mixture of macrocyclic precursor 1, 3-(thiophen-2-yl)-1H-quinoxalin-2-one 2a (1.1 equiv.), and triphenylphosphine (2 equiv.) in THF was added DIAD (2 equiv.) dropwise at 0° C. The resulting mixture was held at 0° C. for 15 min. before being warmed to room temperature. After 18 hours, the mixture was concentrated under vacuum and the residue was purified by chromatography eluting with 60% EtOAc in hexanes to give 2b as a clear oil (100 mg, 99%).

MS (found): 704.4 (M+H). H$^1$-NMR [CDCl$_3$, δ (ppm)]: 8.6 (d, 1H), 8.0 (d, 1H), 7.8 (d, 1H), 7.6 (m, 2H), 7.5 (d, 2H), 7.2 (t, 1H), 7.0 (brs, 1H), 6.0 (brt, 1H), 5.5 (m, 1H), 5.3 (brd, 1H), 5.2 (t, 1H), 5.0 (m. 1H), 4.6 (brt, 1H), 4.1-4.3 (m, 3H), 3.1 (m, 1H), 5.3 (m, 1H), 2.1-2.3 (m, 2H), 1.3 (brs, 9H), 1.2 (t, 3H).

Step 2B. Amine Deprotection.

The title compound of Step 2A (82 mg, 0.116 mmol) was treated with HCl (4 M in dioxane, 3 mL, 12 mmol). The reaction mixture was stirred at room temperature for 2 h until LCMS showed the complete consumption of starting material. The solvent was removed in vacuo.

Step 2C. Chloroformate Reagent

The chloroformate reagent 2C was prepared by dissolving 0.22 mmol of cyclopentanol in THF (5 ml) and adding 0.45 mmol of phosgene in toluene (20%). The resulting reaction mixture was stirred at room temperature for 2 hours and the solvent was removed in vacuo. To the residue was added DCM and subsequently concentrated to dryness twice in vacuo yielding chloroformate reagent 2C.

Step 2D. Carbamate Formation

The resulting residue from step 2B was dissolved in DCM (3 mL) then treated with cyclopentyl chloroformate prepared in step 2C (0.22 mmol) and iPr$_2$NEt (0.35 mL, 2 mmol). The reaction mixture was stirred for 2.5 h. Ethyl acetate (15 mL) was added to the solution. The mixture was washed with saturated aqueous NaHCO3 solution, Water and brine consequently. The organic layer was dried over anhydrous sodium sulfate. The organic phase was then filtered, concentrated in vacuo and subsequently purified by flash chromatography (Ethyl acetate/hexanes 1:2) to give 60.0 mg of the ester. MS (ESI) m/z 716.31 (M+H)$^+$.

Step 2E. Hydrolysis of the Ester

The ester from step 2D and lithium hydroxide (10 equiv.) in THF/MeOH/H$_2$O (2:1:0.5) was stirred at room temperature for 20 hours. The excess solvents were evaporated in vacuo, and the resulting residue was diluted with water and acidified to pH ~5. The mixture was extracted with EtOAc (2×). The combined organic extracts were washed once with brine, dried (MgSO$_4$), filtered and concentrated in vacuo to give an oily residue, which was purified by column chromatography eluting with 2-10% methanol-chloroform to give the title compound (42.0 mg 55% for 3 steps).

MS (ESI) m/z 688.37 (M+H)$^+$. $^{13}$C-NMR (125 MHz, CD$_3$OD): δ 174.6, 173.5, 173.0, 156.7, 152.9, 141.1, 140.0, 139.2, 138.8, 133.4, 130.8, 130.1, 129.3, 128.0, 127.2, 126.7, 126.3, 77.5, 76.2, 59.7, 53.3, 52.6, 40.3, 34.8, 34.4, 32.4, 32.2, 32.1, 30.8, 27.5, 27.4, 26.4, 23.6, 23.3, 23.0, 22.3.

Step 2F. Acyl Aminotetrazole Formation

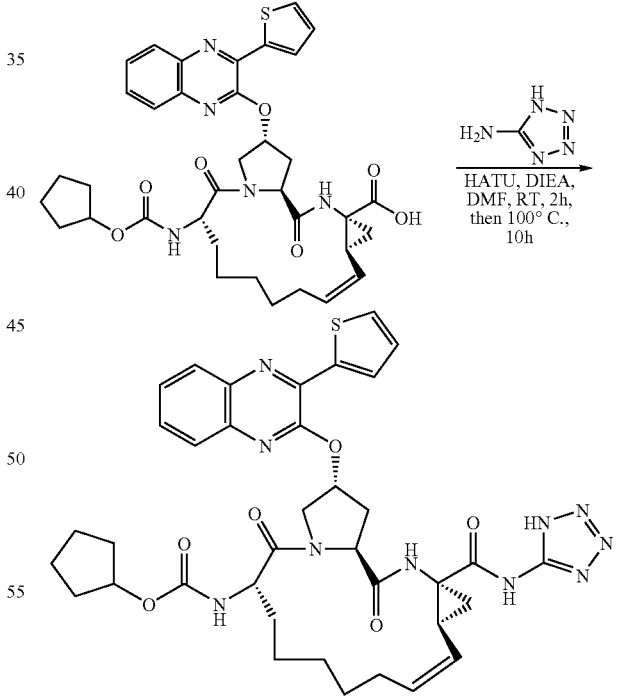

Compound of step 2E (25.0 mg, 0.036 mmol), 5-aminotetrazole (6.0 mg, 0.07 mmol), HATU (16 mg, 0.045 mmol), and DIEA (9.0 mg, 0.07 mmol) were dissolved dissolved in 0.5 ml anhydrous DMF. The mixture was stirred at RT for 1 hour and was heated to 100° C. for 10 hours. The reaction was cooled down and 10 ml ethyl acetate was added to the solution. The mixture was washed with saturated aqueous NaHCO3 solution, Water and brine consequently. The organic layer was dried over anhydrous sodium sulfate. The organic phase was then filtered, concentrated in Vacuo and subsequently purified by HPLC (40-90% Acetonitrile in water) to give 18.0 mg (60%) of the title compound.

MS (ESI) m/z 755.2 (M+H)⁺. ¹H-NMR (400 MHz, CD₃OD): δ 9.08 (1H, s), 8.17 (1H, d, J=3.2 Hz), 7.97 (1H, d, J=6.0 Hz), 7.86 (1H, d, J=6.4 Hz), 7.61-7.69 (3H, m), 7.19 (1H, t, J=3.4 Hz), 6.18 (1H, s), 5.65 (1H, dd, J=7.2, 15.2 Hz), 5.30 (1H, t, J=7.6 Hz), 4.85 (1H, dd, J=6.0, 8.0 Hz), 4.50 (1H, m), 4.21 (1H, m), 4.08 (1H, dd, J=2.6, 9.2 Hz), 2.82 (1H, m), 2.69 (2H, m), 2.51 (1H, dd, J=6.8, 14 Hz), 1.79 (3H, m), 1.23-1.60 (17 H, m). ¹³C-NMR (100 MHz, CD₃OD): δ 177.4, 173.9, 169.5, 156.6, 153.0, 141.2, 140.0, 138.8, 134.6, 130.7, 130.0, 129.3, 128.1, 128.0, 127.2, 126.7, 125.7, 77.5, 76.2, 60.2, 53.4, 52.7, 43.1, 34.9, 32.4, 32.2, 32.0, 31.0, 27.4, 26.9, 26.3, 23.4, 23.3, 22.2.

Example 3

Compound of Formula XV, wherein

A = 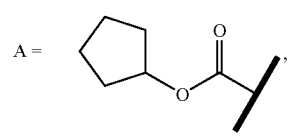

Q = 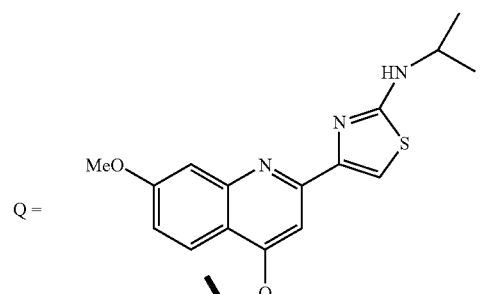

G = 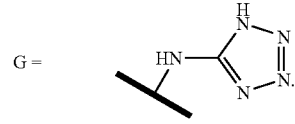

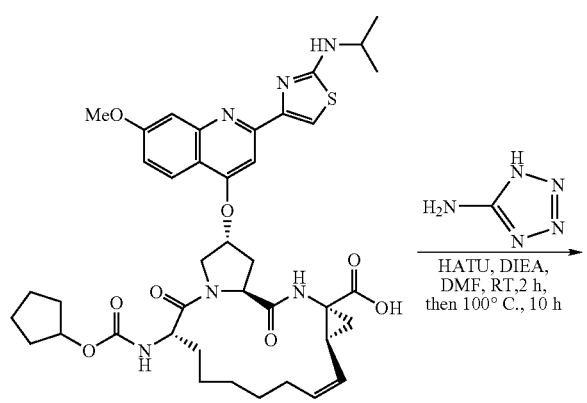

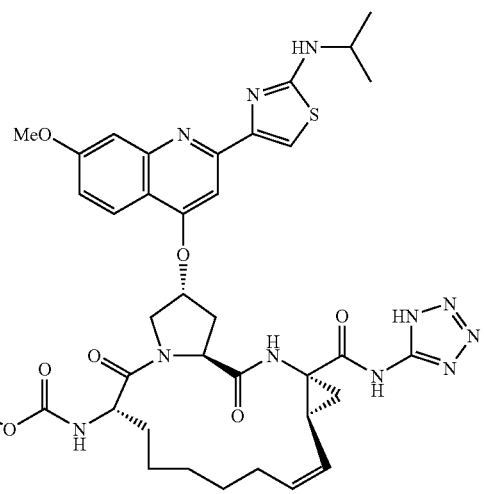

The title compound was prepared following the procedure described in Example 2 by starting with the corresponding Quinoline derivative in the Mitsunobu reaction.

MS (ESI) m/z 842.3 (M+H)⁺.

Example 4

Compound of Formula XV, wherein

A = 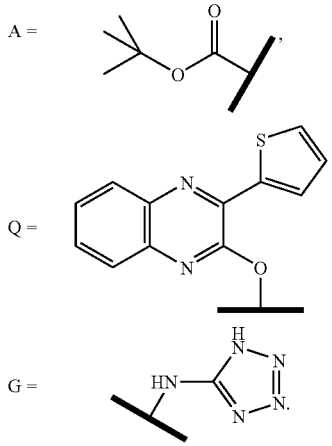

Q = 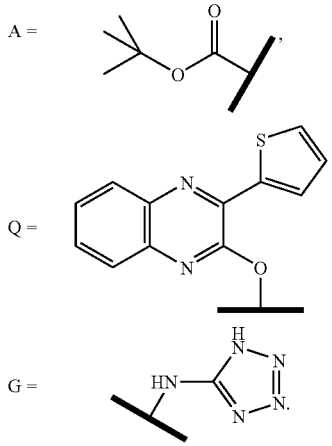

G = 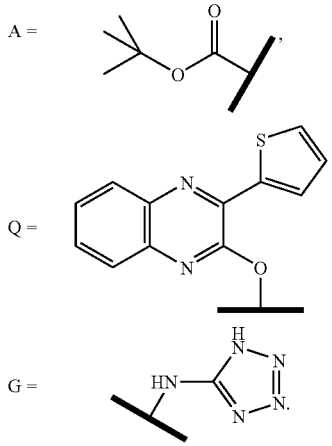

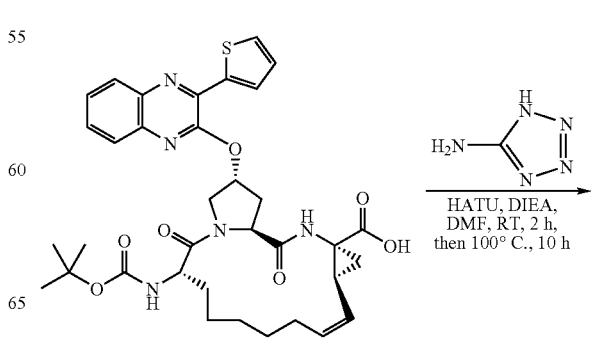

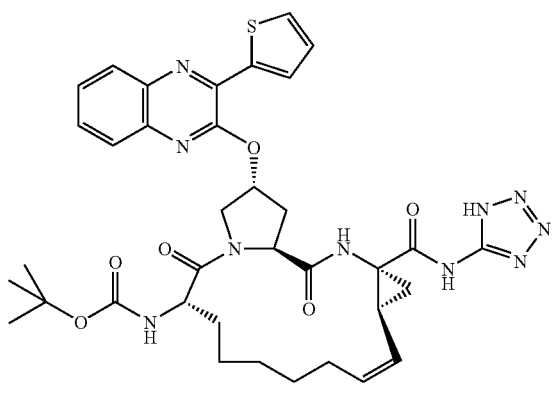

Step 4A. The title compound of step 2A was hydrolyzed by the procedure set forth in step 2E to give the title compound (87%).

MS (found): 676.3 $^1$H-NMR [CD$_3$OD, δ (ppm)]: 8.14 (1H), 7.96 (1H), 7.86 (1H), 7.65 (1H), 7.62 (1H), 7.59 (1H), 7.19 (1H), 6.07 (1H), 5.53 (1H), 5.52 (1H), 4.81 (1H), 4.75 (1H), 4.23 (1H), 4.12 (1H), 2.65-2.75 (2H), 2.52 (1H), 2.21 (1H), 1.97 (1H), 1.80 (1H), 1.62 (2H), 1.54 (1H), 1.47 (2H), 1.44 (2H), 1.41 (2H), 1.09 (9H). $^{13}$C-NMR [CD$_3$OD, δ (ppm)]: 176.2, 174.1, 173.4, 156.0, 152.9, 141.0, 139.6, 138.9, 138.6, 131.5, 130.6, 130.0, 129.3, 128.1, 127.8, 127.1, 126.6, 78.6, 76.1, 59.8, 53.3, 52.3, 41.4, 34.5, 32.3, 30.0, 27.5, 27.4, 27.2 (3C), 26.1, 22.6, 22.4.

Step 4B. The title compound was prepared from the compound of step 4A following the procedure described in Example 2, step 2F.

MS (ESI) m/z 743.38 (M+H)$^+$.

Example 5

Compound of Formula XV, wherein

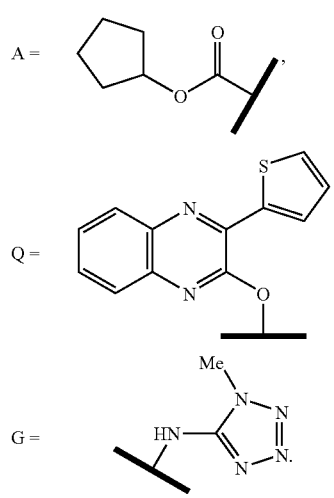

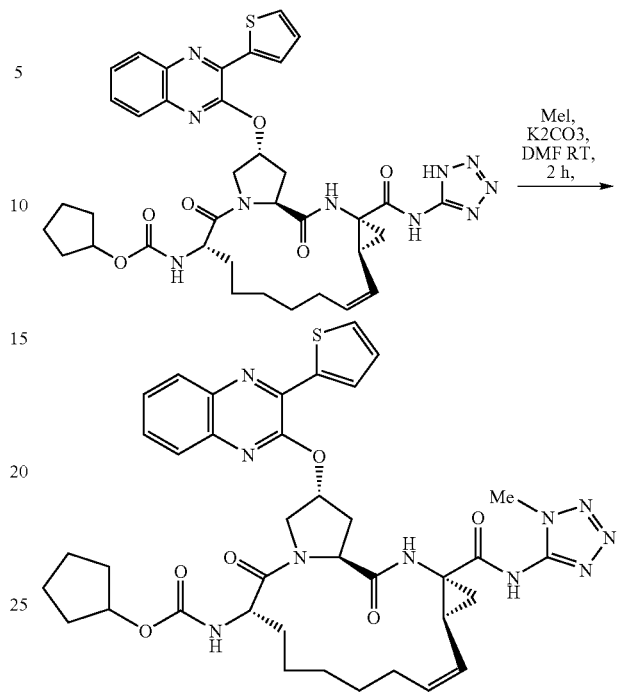

The compound from Example 2 (13.0 mg, 0.017 mmol), K2CO3 (5.0 mg, 0.035 mmol), were dissolved in 0.5 ml anhydrous DMF. To the resulting solution was added Iodomethane (5.0 mg, 0.035 mmol) at RT. The mixture was stirred at RT for 1 hour. The reaction was quenched by adding 10 ml ethyl acetate and 5 ml water. The mixture was washed with saturated aqueous NaHCO3 solution, Water and brine consequently. The organic layer was dried over anhydrous sodium sulfate. The organic phase was then filtered, concentrated in Vacuo and subsequently purified by HPLC (40-90% Acetonitrile in water) to give 6.0 mg (50%) of the desired compound.

MS (ESI) m/z 769.2 (M+H)$^+$.

Example 6

Compound of Formula XV, wherein

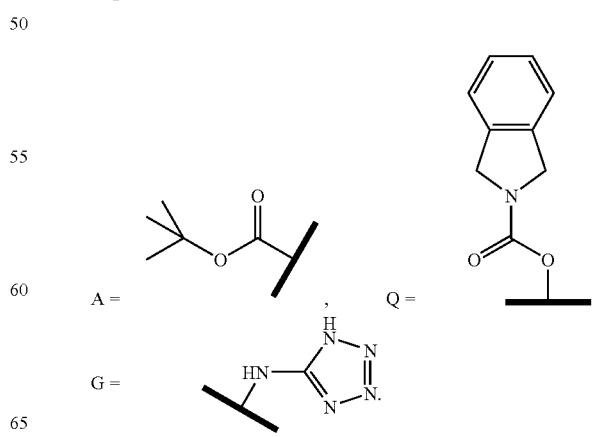

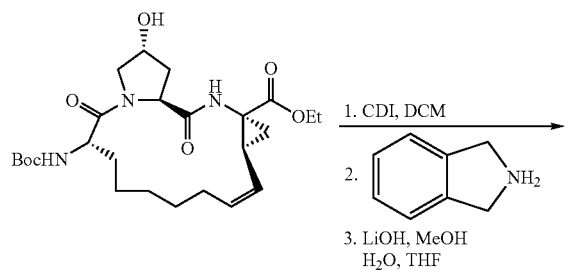

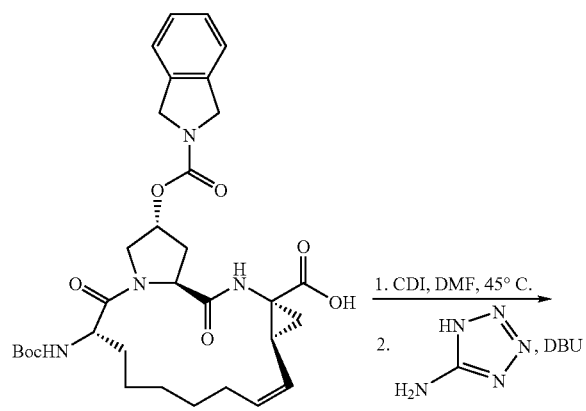

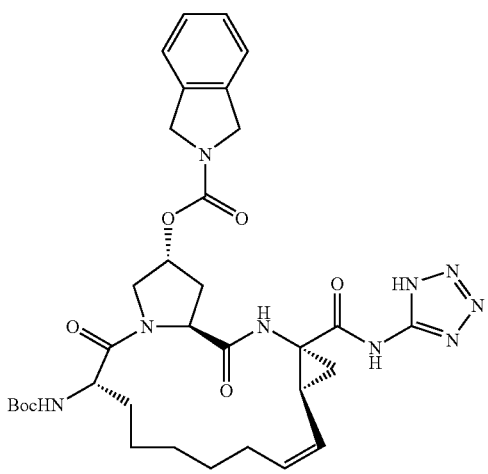

Step 6A. Compound of Formula XV, wherein

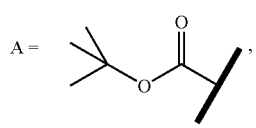

Q=OH G=OEt.

The title compound was prepared following Example-1 by starting with the commercially available trans-L-hydroxyproline methyl ester in step 1A.

Step 6B. Compound of Formula XV, wherein

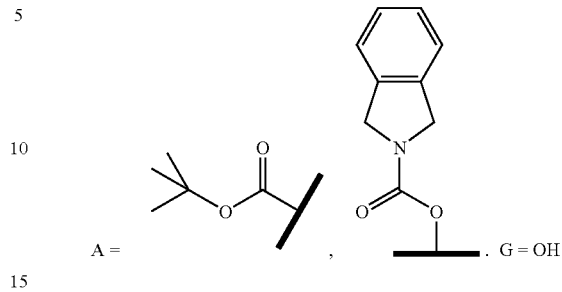

The alcohol from step 6A (200 mg, 0.40 mmol) was condensed with CDI (79 mg, 0.49 mmol) in 5 mL dichloromethane at rt. Once this coupling was complete as confirmed by MS analysis, isoindoline (145 mg, 1.21 mmol) was added and the resulting mixture was stirred overnight. The reaction mixture was diluted with dichloromethane (20 mL) and washed with 1N aq. HCl (20 mL) and brine (20 mL). The organic portion was then dried ($Na_2SO_4$), filtered, and concentrated in vacuo. The crude oil was purified via flash chromatography (silica gel) using dichloromethane/EtOAc/acetone (60:20:1) as eluent to afford the corresponding carbamate (220 mg, 85%) as a white solid.

Once the carbamate portion was installed, ester hydrolysis was carried out in standard fashion using LiOH in a THF/MeOH/water (1.5, 0.5, 0.5 mL, respectfully) solvent mixture. Upon completion, the reaction mixture was diluted with 50 mL DCM and 5 mL water, which was acidified with 1N aq. HCl. The layers were separated and the aqueous portion was washed three additional times with 10 mL DCM. The organic portions were combined and washed once with brine (20 mL). Finally, the organic layer was dried ($Na_2SO_4$), filtered, and concentrated in vacuo. The crude acid was carried on to the coupling step without any further purification.

Step 6C. Compound of Formula XV, wherein

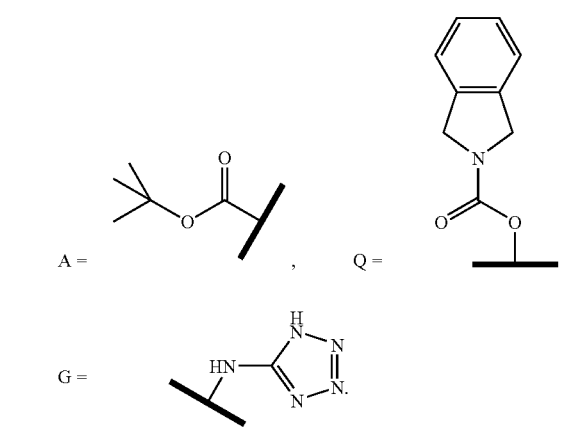

Carboxylic acid from step 6B (50 mg, 0.082 mmol) was treated with CDI (16 mg, 0.098 mmol) in 2 mL DMF at 45° C. for 1 hr. The activated intermediate was then subjected to aminotetrazole (14 mg, 0.16 mmol) and DBU (19 mg, 0.12 mmol). After stirring overnight, the reaction was diluted with 50 mL EtOAc and washed with water (3×10 mL) and brine (1×20 mL). The organic portion was dried (Na₂SO₄), filtered, and concentrated in vacuo. The crude material was purified via preparative HPLC to yield title compound (32 mg, 60%).

MS (ESI) m/z 678.19 (M+H)⁺. ¹H-NMR (500 MHz, CDCl₃): δ 11.49 (1H, s), 7.36 (1H, m), 7.28-7.23 (2H, m), 7.17-7.16 (2H, m), 5.70 (1H, dd, J=17.0, 9.5 Hz), 5.59 (1H, dd, J=17.0, 10.0 Hz), 5.41 (1H, bs), 5.35 (1H, t, J=9.5 Hz), 5.31-5.29 (1H, m), 5.23 (1H, t, J=9.5 Hz), 5.18 (1H, m), 4.78-4.70 (2H, m), 4.66-4.60 (1H, m), 4.44-4.40 (1H, m), 4.25-4.19 (1H, m), 4.15-4.13 (1H, m), 3.90 (1H, dd, J=11.5, 5.0 Hz), 3.85 (1H, dd, J=11.5, 3.5 Hz), 2.70 (1H, ddd, J=13.5, 6.0, 6.0 Hz), 2.62-2.50 (2H, m), 2.38-2.18 (4H, m), 2.10-2.02 (1H, m), 1.88-1.20.

Example 7

Compound of Formula XV, wherein

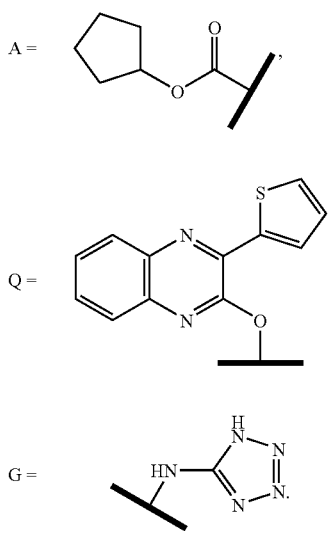

The title compound was prepared from the compound of Example 2, step 2E following the procedure described in Example 2, step 2F by using aminotriazole in the place of aminotetrazole.

MS (ESI) m/z 754.36 (M+H)⁺.

Example 8

Compound of Formula XV, wherein

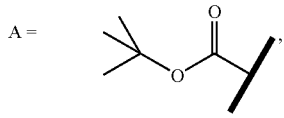

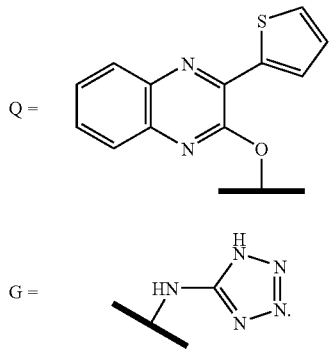

The title compound is prepared from the compound of Example 4, step 4A following the procedure described in Example 2, step 2F by using aminotriazole in the place of aminotetrazole.

Example 9

Compound of Formula XV, wherein

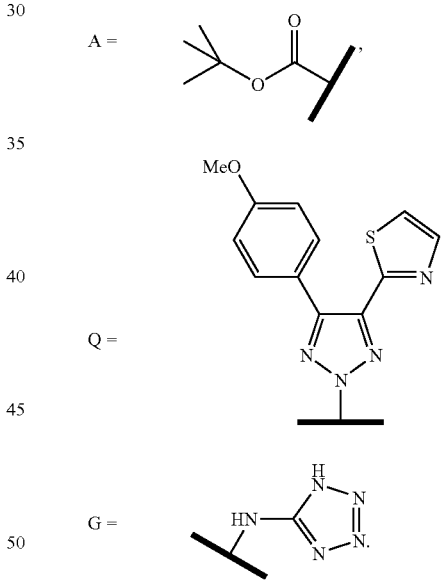

The title compound is made by following Example 4 using the corresponding triazole in the Mitsunobu reaction in place of the quinoxalin-2-one.

Additional compounds (Example 10-25) of the present invention that may be prepared via methods described in step 2F using the corresponding carboxylic acids. The corresponding carboxylic acids maybe prepared via methods described in Schemes 2-8 or in Examples 2-10, or the detailed procedure of making such acids could be found in U.S. published patent application US2002/0037998; PCT published application WO 00/59929; and commonly assigned U.S. Ser. No. 10/384,120 (filed Mar. 7, 2003), Ser. No. 10/418,759 (filed Apr. 18, 2003), Ser. No. 10/360,947 (filed Feb. 7, 2003) and Ser. No. 10/365,854 (filed Feb. 13, 2003).

TABLE 1
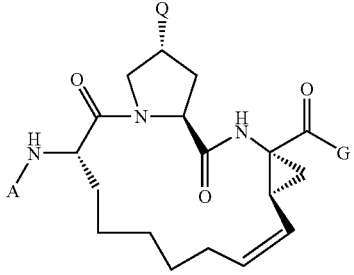
(XV)
| Example # | A | Q | G |
|---|---|---|---|
| 10 | 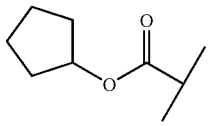 | 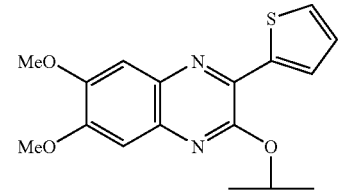 | 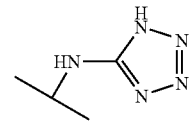 |
| 11 | 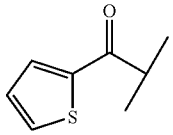 | 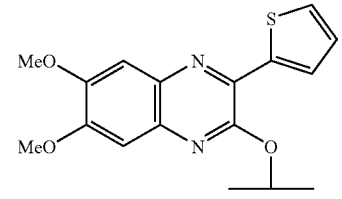 | 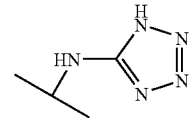 |
| 12 | 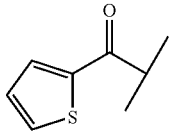 | 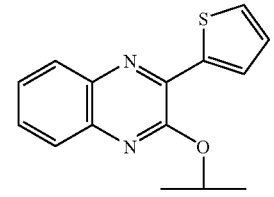 | 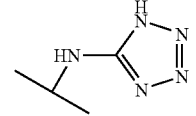 |
| 13 | 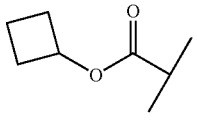 | 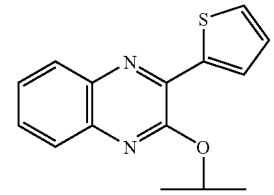 | 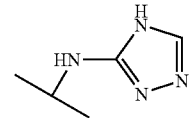 |
| 14 | 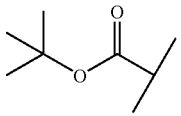 | 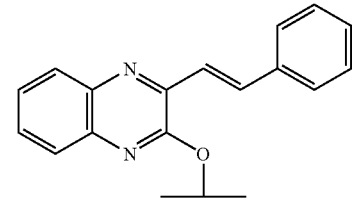 | 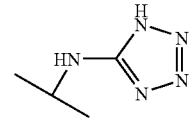 |
| 15 | 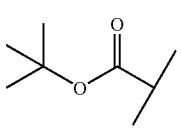 | 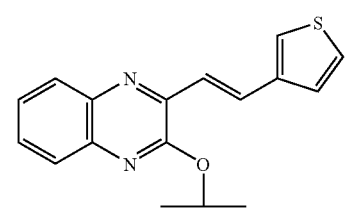 | 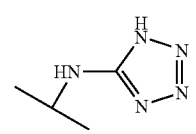 |

TABLE 1-continued (XV)

| Example # | A | Q | G |
|---|---|---|---|
| 16 | tert-butyl 2-methylpropanoate group | 3-(2-(thiazol-2-yl)ethyl)-2-(propan-2-yloxy)quinoxaline | N-isopropyl-1H-tetrazol-5-amine |
| 17 | cyclopentyl 2-methylpropanoate group | 5,8-dimethoxy-3-(thiophen-2-yl)-2-(propan-2-yloxy)quinoxaline | N-isopropyl-1H-tetrazol-5-amine |
| 18 | cyclopentyl 2-methylpropanoate group | 6,7-dichloro-3-(thiophen-2-yl)-2-(propan-2-yloxy)quinoxaline | N-isopropyl-1H-tetrazol-5-amine |
| 19 | cyclopentyl 2-methylpropanoate group | 6-methoxy-3-(thiophen-2-yl)-2-(propan-2-yloxy)quinoxaline | N-isopropyl-1H-tetrazol-5-amine |
| 20 | cyclopentyl 2-methylpropanoate group | 7-methoxy-3-(thiophen-2-yl)-2-(propan-2-yloxy)quinoxaline | N-isopropyl-1H-tetrazol-5-amine |
| 21 | 1-(1H-pyrrol-2-yl)-2-methylpropan-1-one | 3-(thiophen-2-yl)-2-(propan-2-yloxy)quinoxaline | N-isopropyl-1H-tetrazol-5-amine |

TABLE 1-continued

Example 26

Compound of Formula XVI, wherein

A = 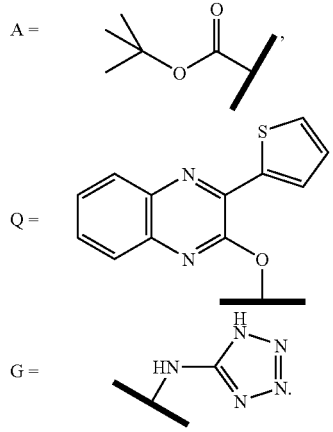

Q =

G =

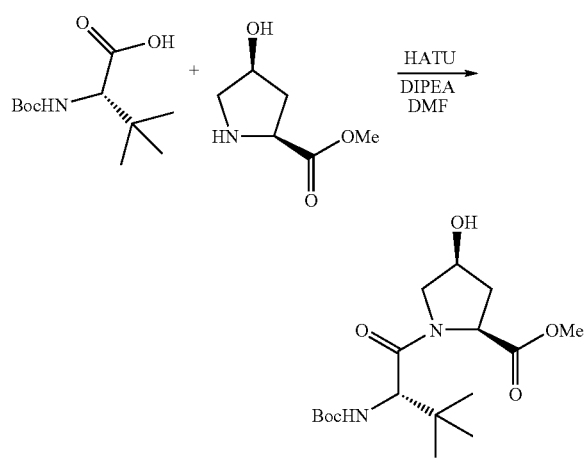

Step 26A. To a solution of Boc-L-tert-leucine (4.544 g, 19.65 mmol), cis-L-hydroxyproline methyl ester (19.65 mmol) and DIPEA (10.3 ml, 59.1 mmol) in DMF (80 ml) at 0° C. was added in portions HATU (7.84 g, 20.6 mmol). The mixture was stirred at rt for 18 h, diluted with EtOAc and washed with half-sat.-aq. NaCl four times. The organic phase was dried over anhydrous MgSO₄, filtered, and then concentrated in vacuo. The resudue was purified by silica gel chromatography (Hexane/EtOAC=1:1 to 1:2) to afford the desired compound (7.8 g). MS (ESI): m/e 359.24 (M+H).

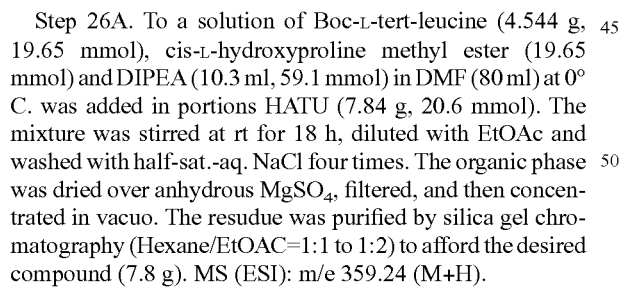

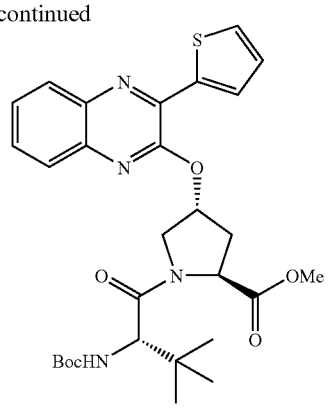

Step 26B. To a mixture of the above compound (1.363 g, 3.803 mmol), 3-(thiophen-2-yl)-1H-quinoxalin-2-one (0.868 g, 3.803 mmol)) and triphenylphosphine (2.0 g, 7.6 mmol) in THF at 0° C. was added dropwise DIAD (1.5 ml, 7.6 mmol). The resulting mixture was held at 0° C. for 15 min. before being warmed to room temperature. After 18 hours, the mixture was concentrated under vacuum and the residue was purified by chromatography (Hexane/EtOAC=9:1 to 7:3) to give the desired compound (1.8 g). MS(ESI): m/e 569.27 (M+H)

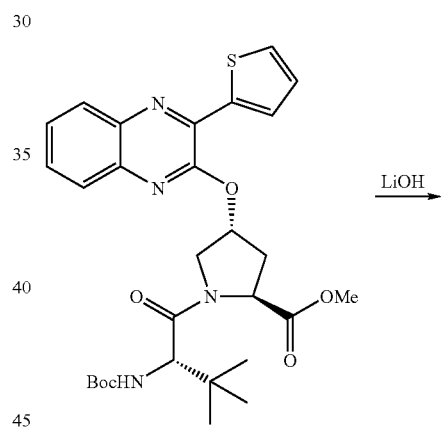

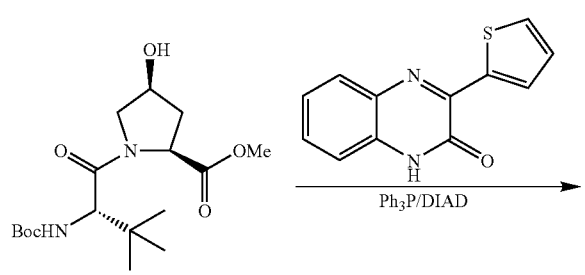

Step 26C. To a solution of compound from Step 26B (1.77 g, 3.11 mmol) in THF/MeOH/H₂O (36 ml-18 ml-18 ml) was added lithium hydroxide mono hydrate (0.783 g, 18.6 mmol). The mixture was stirred at room temperature for 20 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford the title compound (95%). MS(ESI): m/e 555.26 (M+H).

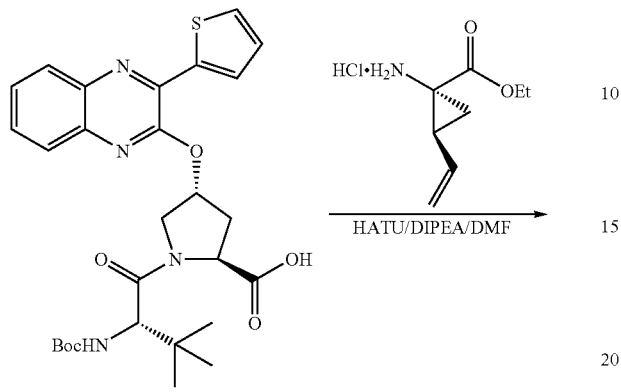

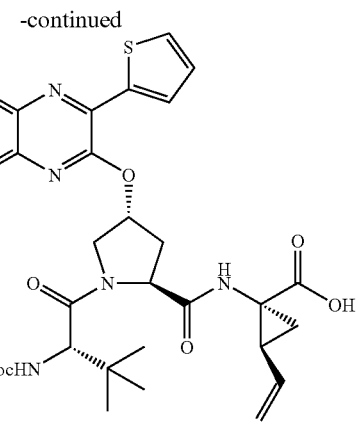

Step 26D. To a solution of compound from Step 26C (98 mg, 0.177 mmol), (1R,2S)-1-Amino-2-vinyl-cyclopropan-ecarboxylic acid ethyl ester HCl salt (34 mg, 0.177 mmol) and DIPEA (0.125 ml, 0.71 mmol) in DMF (3 ml) at 0° C. was added HATU (81 mg, 0.212 mmol). The mixture was stirred at rt for 18 h, diluted with EtOAc and washed with half-sat.-aq. NaCl four times. The organic phase was dried over anhydrous MgSO$_4$, filtered, and then concentrated in vacuo. The resudue was purified by silica gel chromatography (Hexane/EtOAC=3:1 to 2:1) to afford the title compound (86 mg). MS (ESI): m/e 692.32 (M+H).

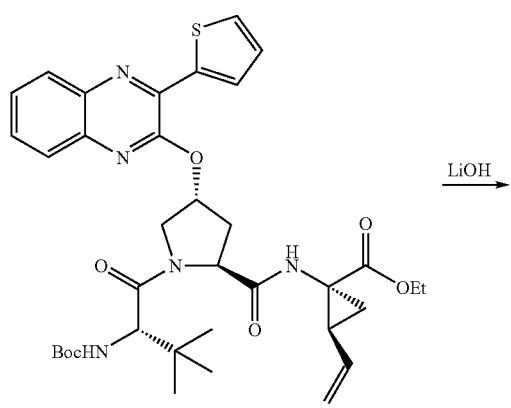

Step 26E. To a solution of compound from Step 26D (79 mg, 0.114 mmol) in THF/MeOH/H$_2$O (2 ml-1 ml-0.5 ml) was added aqueous lithium hydroxide (1N, 0.6 ml, 0.6 mmoL). The mixture was stirred at room temperature for 20 hours. Most organic solvents were evaporated in vacuo, and the resulting residue was diluted with water and acidified to pH 5 to 6. The mixture was extracted with EtOAc three times. The combined organic extracts were dried (MgSO$_4$), filtered and concentrated in vacuo to afford the title compound (73 mg). MS(ESI): m/e 664.20 (M+H).

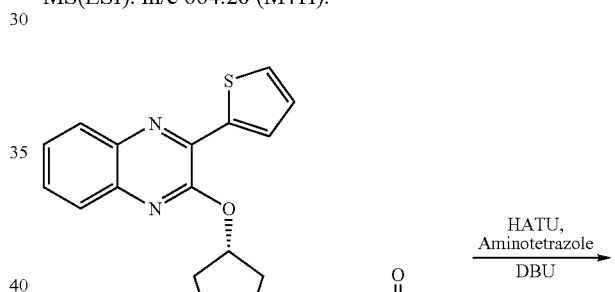

Step 26F. The title compound was prepared from the compound of step 26E following the procedure described in Example 2, step 2F.

MS (ESI) m/z 731.44 (M+H); 689.41 (M−N$_3$)

Additional compounds (Example 27-49) of the present invention that may be prepared via methods described in Example 26 using the corresponding proline substitutions (step 26B). The general methods for such substitution is either illustrated in Schemes 2-8 or in Examples 2-25 by substituting the macrocyclic core structures with the acyclic structure from Step 26A.
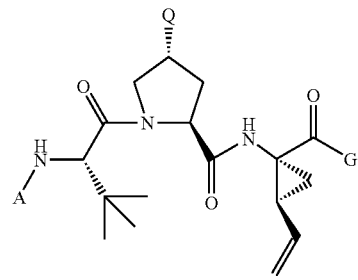
(XVI)

(XVI)
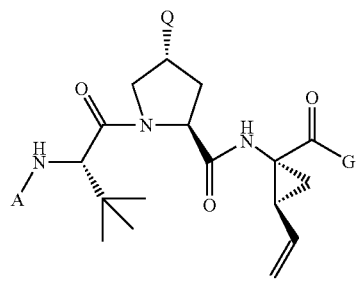
| Example# | A | Q | G |
|---|---|---|---|
| 31 | 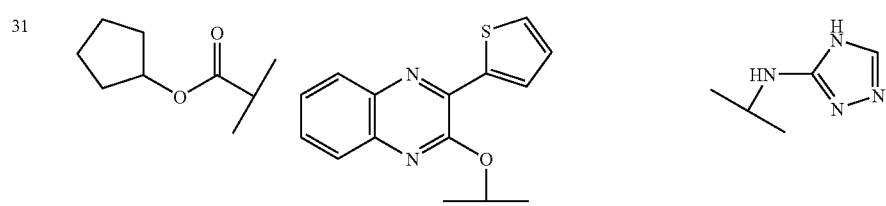 | | |
| 32 | 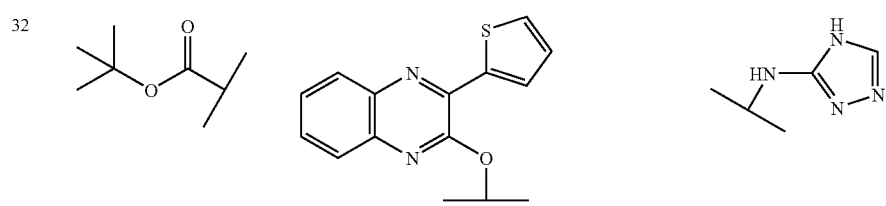 | | |
| 33 | 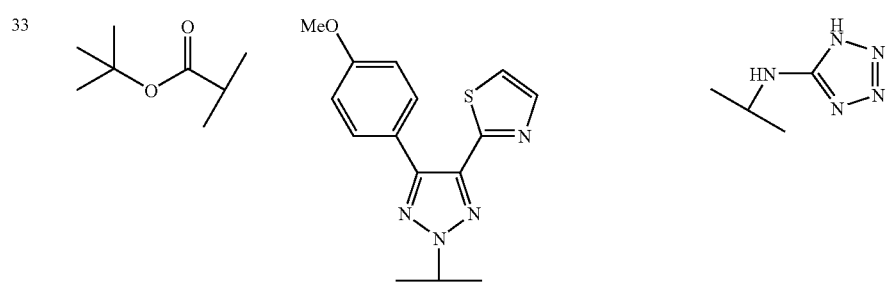 | | |
| 34 | 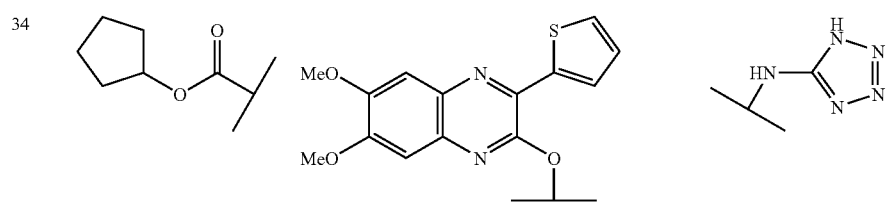 | | |
| 35 | 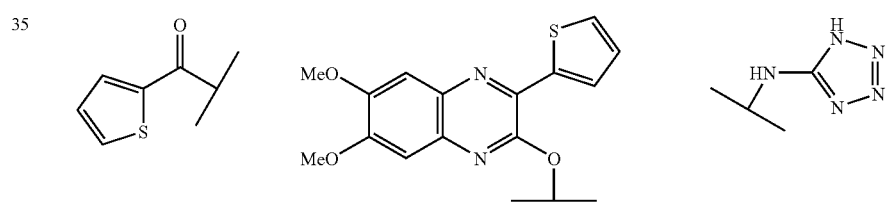 | | |

-continued
(XVI)
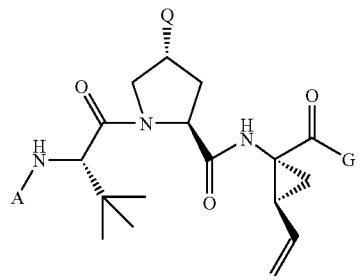
| Example# | A | Q | G |
|---|---|---|---|
| 36 | 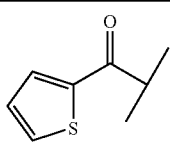 | 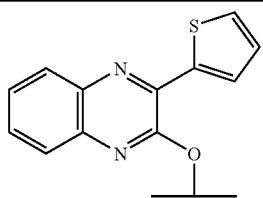 | 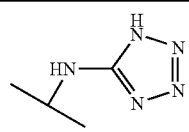 |
| 37 | 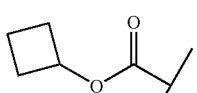 | 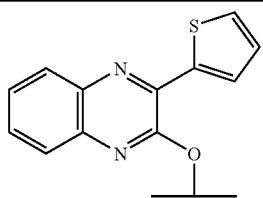 | 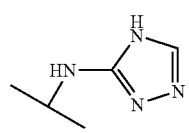 |
| 38 | 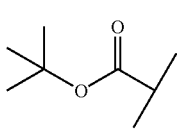 | 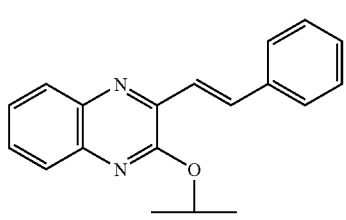 | 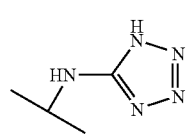 |
| 39 | 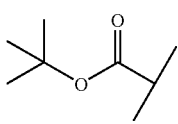 | 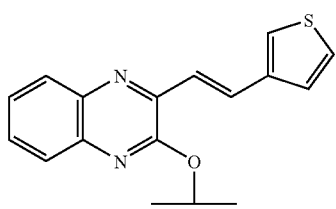 | 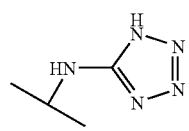 |
| 40 | 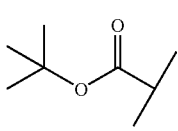 | 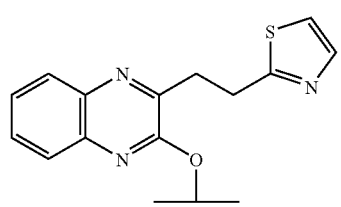 | 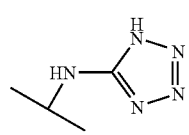 |
| 41 | 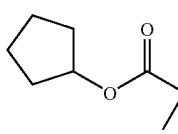 | 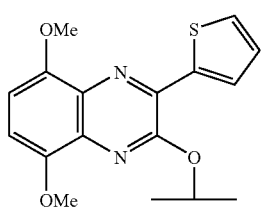 | 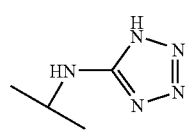 |

-continued
(XVI)
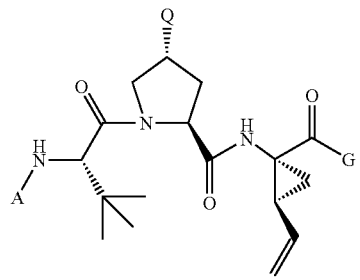
| Example# | A | Q | G |
|---|---|---|---|
| 42 | 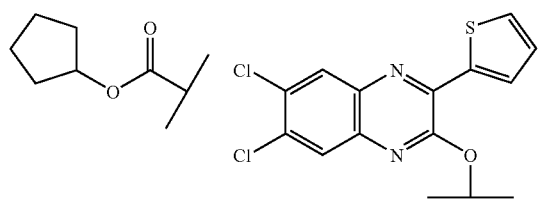 | | |
| 43 | 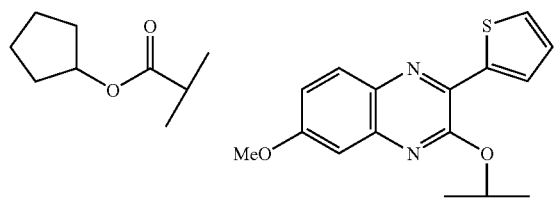 | | |
| 44 | 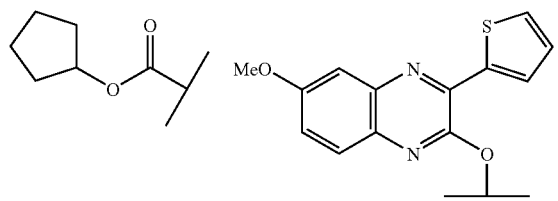 | | |
| 45 | 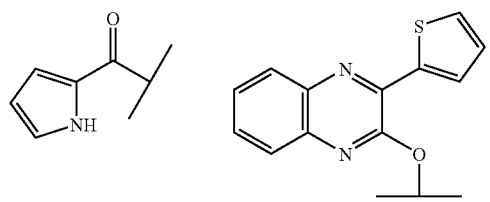 | | |
| 46 | 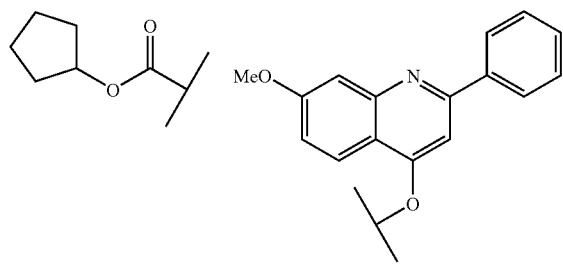 | | |

-continued (XVI)

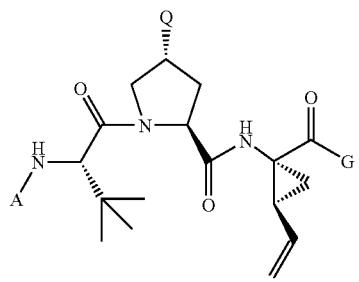

| Example# | A | Q | G |
|---|---|---|---|
| 47 | 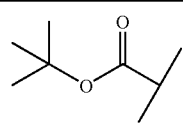 | 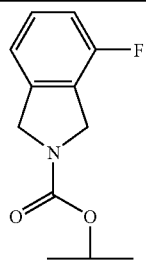 | 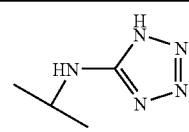 |
| 48 | 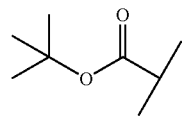 | 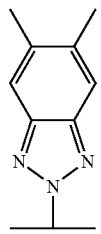 | 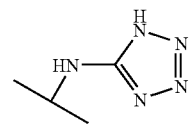 |
| 49 | 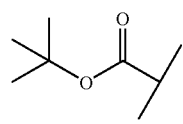 | 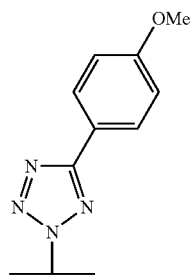 | 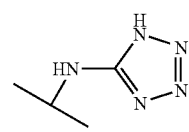 |

The compounds of the present invention exhibit potent inhibitory properties against the HCV NS3 protease. The following examples describe assays in which the compounds of the present invention can be tested for anti-HCV effects.

Example 50

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 μM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-NH$_2$, AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh 2 (Anaspec 25346, MW 913.1) Ac-Asp-Glu-Dif-Cha-Cys-OH, are used as reference compounds.

IC50 values are calculated using XLFit in ActivityBase (IDBS) using equation 205: y=A+((B−A)/(1+((C/x)^D))).

Example 51

Cell-Based Replicon Assay

Quantification of HCV replicon RNA in cell lines (HCV Cell Based Assay) Cell lines, including Huh-11-7 or Huh 9-13, harboring HCV replicons (Lohmann, et al Science 285: 110-113, 1999) are seeded at $5 \times 10^3$ cells/well in 96 well plates and fed media containing DMEM (high glucose), 10% fetal calf serum, penicillin-streptomycin and non-essential amino acids. Cells are incubated in a 7.5% $CO_2$ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

HCV Forward primer "RBNS5bfor"

5'GCTGCGGCCTGTCGAGCT (SEQ ID NO: 1):

HCV Reverse primer "RBNS5Brev"

5'CAAGGTCGTCTCCGCATAC (SEQ ID NO 2).

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
                                     (SEQ ID NO: 3)
   5' FAM-CGAAGCTCCAGGACTGCACGATGCT-TAMRA
```

FAM=Fluorescence reporter dye.

TAMRA:=Quencher dye.

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, are contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines The effect of a specific anti-viral compound on HCV replicon RNA levels in Huh-11-7 or 9-13 cells is determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells are seeded at $5 \times 10^3$ cells/well in a 96 well plate and are incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above are then incubated at 37° C. for 3 days (primary screening assay) or 4 days (IC50 determination). Percent inhibition is defined as:

$$\% \text{ Inhibition}=[100-((S-C2)/C1-C2))]\times 100$$

where

S=the ratio of HCV RNA copy number/GAPDH RNA copy number in the sample;

C1=the ratio of HCV RNA copy number/GAPDH RNA copy number in the 0% inhibition control (media/1% DMSO); and C2=the ratio of HCV RNA copy number/GAPDH RNA copy number in the 100% inhibition control (100 IU/ml Interferon-alpha 2b).

The dose-response curve of the inhibitor is generated by adding compound in serial, three-fold dilutions over three logs to wells starting with the highest concentration of a specific compound at 10 uM and ending with the lowest concentration of 0.01 uM. Further dilution series (1 uM to 0.001 uM for example) is performed if the IC50 value is not in the linear range of the curve. IC50 is determined based on the IDBS Activity Base program using Microsoft Excel "XL Fit" in which A=100% inhibition value (100 IU/ml Interferon-alpha 2b), B=0% inhibition control value (media/1% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4-6 wells are used to define the 100% and 0% inhibition values.

In the above assays, representative compounds are found to have activity.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the formula (I):

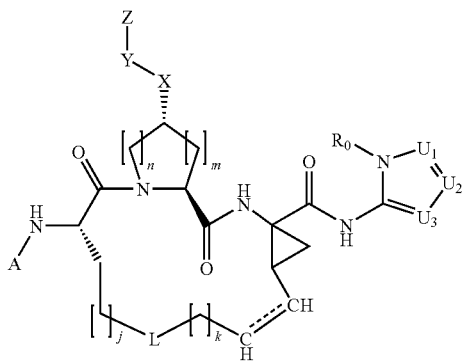

or a pharmaceutically acceptable salt or ester thereof, wherein:

A is selected from H, —(C=O)—O—$R_1$, —(C=O)—$R_2$, —C(=O)—NH—$R_2$, or —S(O)$_2$—$R_1$, —S(O)$_2$NH$R_2$;

$R_1$ is selected from the group consisting of:
(i) aryl;
(ii) substituted aryl;
(iii) heteroaryl;
(iv) substituted heteroaryl;
(v) heterocycloalkyl or substituted heterocycloalkyl;
(vi) —$C_1$-$C_8$ alkyl;
(vii) —$C_2$-$C_8$ alkenyl;
(viii) —$C_2$-$C_8$ alkynyl containing 0, 1, 2, or 3 heteroatoms selected from O, S, or N;
(ix) substituted —$C_1$-$C_8$ alkyl;
(x) substituted —$C_2$-$C_8$ alkenyl;
(xi) substituted —$C_2$-$C_8$ alkynyl containing 0, 1, 2, or 3 heteroatoms selected from O, S or N;
(xii) —$C_3$-$C_{12}$ cycloalkyl;
(xiii) substituted —$C_3$-$C_{12}$ cycloalkyl;
(xiv) —$C_3$-$C_{12}$ cycloalkenyl; and
(xv) substituted —$C_3$-$C_{12}$ cycloalkenyl;

$R_2$ is selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, and N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S and N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;

$R_0$ is H, Me, Et, —OH, or —C(O)NH$_2$;

$U_1$, $U_2$, and $U_3$ are independently selected from:
(i) hydrogen;
(ii) halogen;
(iii) —NO$_2$;
(iv) —CN;
(v) -M-$R_4$, wherein M is absent, O, S, NH, or N$R_5$;
(vi) aryl;
(vii) substituted aryl;
(viii) heteroaryl;
(ix) substituted heteroaryl;
(x) heterocycloalkyl; and
(xi) substituted heterocycloalkyl;

Each $R_4$, $R_5$ is independently selected from:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S, and N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S or N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;

L is selected from —CH$_2$—, —O—, —S—, —S(O)$_2$—, —CO—, —C(O)O—, —C(O)NH—, —CHF—, —CF$_2$—, aryl, substituted aryl, heteroaryl, substituted heteroaryl;

X is selected from the group consisting of:
(i) oxygen;
(ii) sulfur; and
(iii) N$R_4$;

Y is absent or is selected from the group consisting of:
(i) —$C_1$-$C_6$ alkyl containing 0, 1, 2, or 3 heteroatoms selected from O, S, and N, optionally substituted with one or more substituent selected from halogen, aryl, substituted aryl, heteroaryl, and substituted heteroaryl;
(ii) —$C_2$-$C_6$ alkenyl containing 0, 1, 2, or 3 heteroatoms selected from O, S, and N, optionally substituted with one or more substituent selected from halogen, aryl, substituted aryl, heteroaryl, or substituted heteroaryl;
(iii) —$C_2$-$C_6$ alkynyl containing 0, 1, 2, or 3 heteroatoms selected from O, S, and N, optionally substituted with one or more substituent selected from halogen, aryl, substituted aryl, heteroaryl, and substituted heteroaryl;
(iv) —$C_3$-$C_{12}$ cycloalkyl;
(v) substituted —$C_3$-$C_{12}$ cycloalkyl;
(vi) heterocycloalkyl; and
(vii) substituted heterocycloalkyl;

Z is selected from aryl, substituted aryl, heteroaryl, and substituted heteroaryl;

j=0, 1, 2, 3, or 4;
k=1, 2, or 3;
m=1;
n=1; and
----- denotes a carbon-carbon single or double bond.

2. A compound according to claim 1 represented by formula (III):

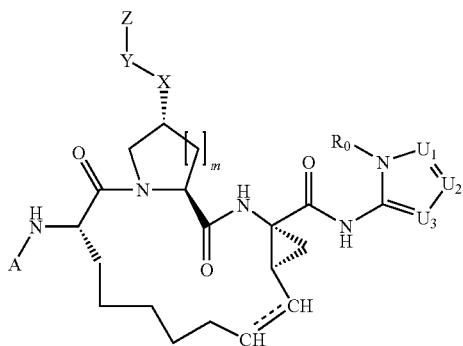

(III)

or a pharmaceutically acceptable salt or ester thereof.

3. A compound according to claim 1 represented by formula (V):

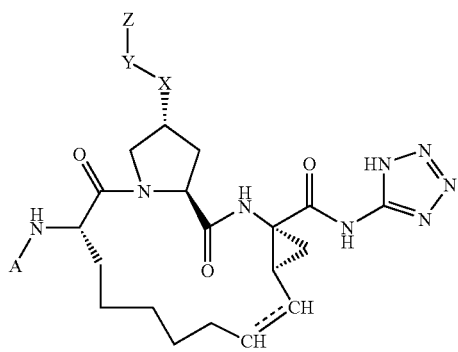

(V)

or a pharmaceutically acceptable salt or ester thereof.

4. A compound according to claim 1 represented by formula (VII):

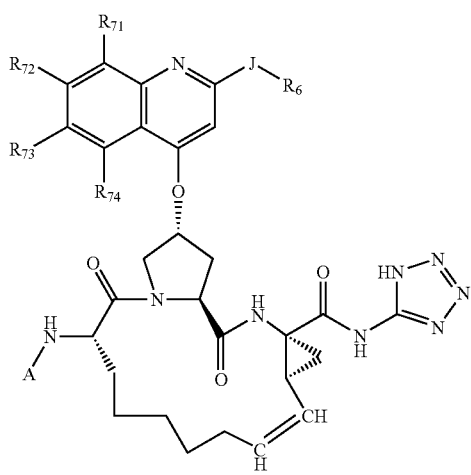

(VII)

or a pharmaceutically acceptable salt or ester thereof, wherein:

$R_6$ is selected from aryl, substituted aryl, heteroaryl, and substituted heteroaryl;

J is absent or selected from O, S, $NR_5$, CO, (CO)$NR_5$, (CO)O, $NR_5$(CO), NH(CO)NH and $NR_5SO_2$; and each $R_{71}$, $R_{72}$, $R_{73}$ and $R_{74}$ is absent or independently selected from:

(i) hydrogen;
(ii) halogen;
(iii) —$NO_2$;
(iv) —CN;
(v) -M-$R_4$, wherein M is absent, or O, S, NH, $NR_5$;
(vi) aryl;
(vii) substituted aryl;
(viii) heteroaryl;
(ix) substituted heteroaryl;
(x) heterocycloalkyl; and
(xi) substituted heterocycloalkyl.

5. A compound according to claim 1 represented by formula (IX):

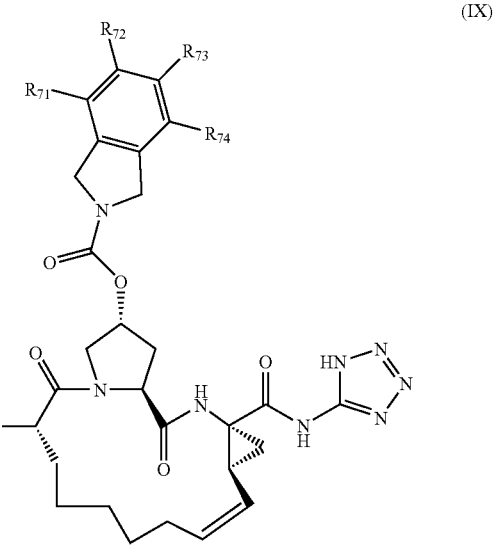

(IX)

or a pharmaceutically acceptable salt or ester thereof, wherein:

each $R_{71}$, $R_{72}$, $R_{73}$, and $R_{74}$ is absent or independently selected from:

(i) hydrogen;
(ii) halogen;
(iii) —$NO_2$;
(iv) —CN;
(v) -M-$R_4$, wherein M is absent, or O, S, NH, $NR_5$;
(vi) aryl;
(vii) substituted aryl
(viii) heteroaryl;
(ix) substituted heteroaryl;
(x) heterocycloalkyl; and
(xi) substituted heterocycloalkyl.

6. A compound according to claim 1 represented by formula (XI):

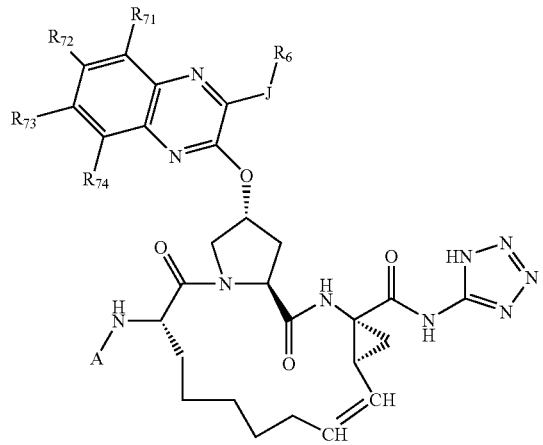

(XI)

or a pharmaceutically acceptable salt or ester thereof, wherein:

$R_6$ is selected from aryl, substituted aryl, heteroaryl, and substituted heteroaryl;

J is absent or selected from O, S, $NR_5$, CO, (CO)$NR_5$, (CO)O, $NR_5$(CO), NH(CO)NH and $NR_5SO_2$; and each $R_{71}$, $R_{72}$, $R_{73}$, and $R_{74}$ is absent or independently selected from:

(i) hydrogen;
(ii) halogen;
(iii) —$NO_2$;
(iv) —CN;
(v) -M-$R_4$, wherein M is absent, or O, S, NH, $NR_5$;
(vi) aryl;
(vii) substituted aryl
(viii) heteroaryl;
(ix) substituted heteroaryl;
(x) heterocycloalkyl; and
(xi) substituted heterocycloalkyl.

7. A compound according to claim 1 represented by formula (XIII):

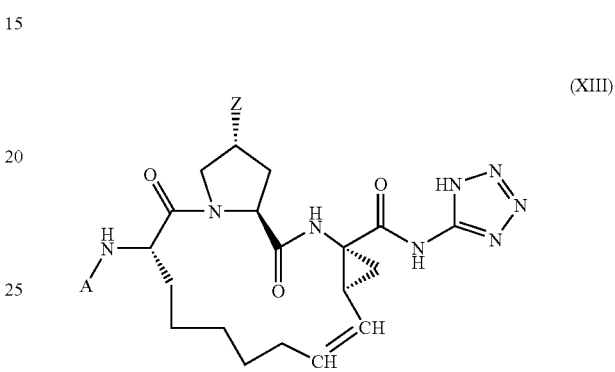

(XIII)

or a pharmaceutically acceptable salt or ester thereof.

8. A compound of claim 1 represented by Formula (XV) selected from group consisting of compounds 2-25 of Table 1 or a pharmaceutically acceptable salt thereof, wherein A, Q and G are defined in Table 1:

TABLE 1

(XV)

| Compound | A | Q | G |
|---|---|---|---|
| 2 | cyclopentyl-O-C(O)- | quinoxalinyl(thiophene)-O- | tetrazolyl-NH- |

TABLE 1-continued
(XV)
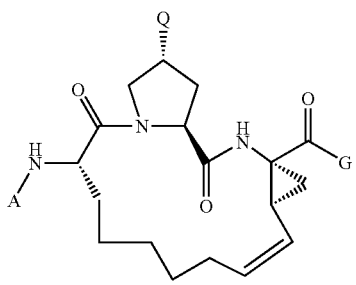
| Compound | A | Q | G |
|---|---|---|---|
| 3 | 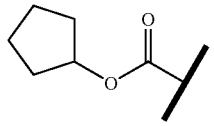 | 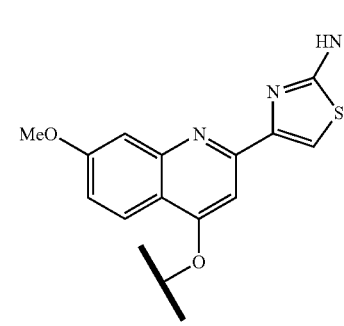 | 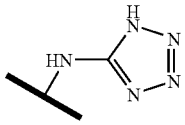 |
| 4 | 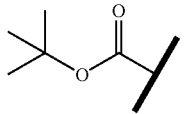 | 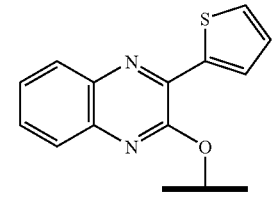 | 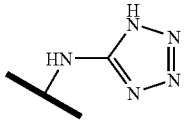 |
| 5 | 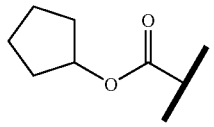 | 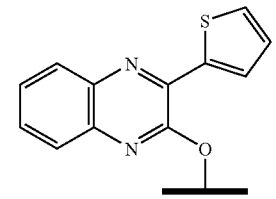 | 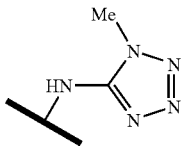 |
| 6 | 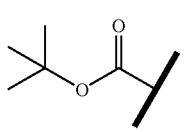 | 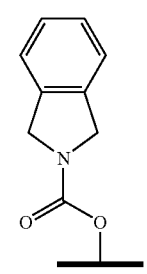 | 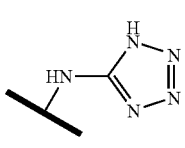 |
| 7 | 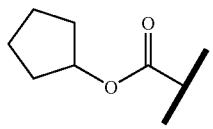 | 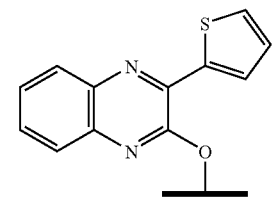 | 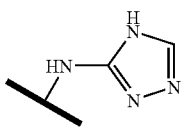 |

TABLE 1-continued
(XV)
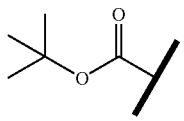
| Compound | A | Q | G |
|---|---|---|---|
| 8 | 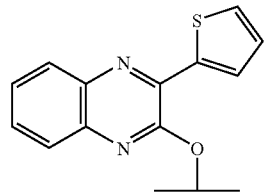 | 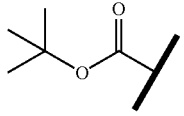 | 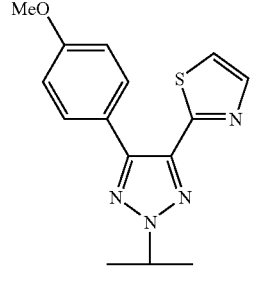 |
| 9 | 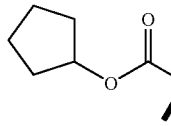 | 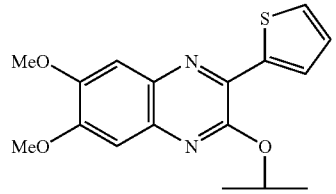 | 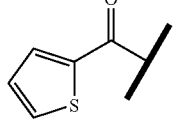 |
| 10 | 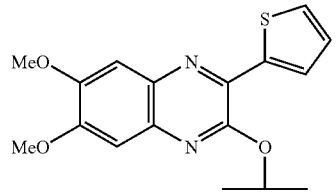 | 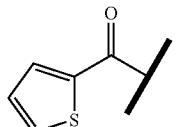 | 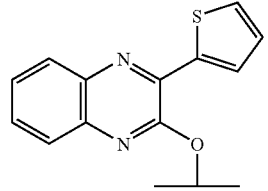 |
| 11 | | | |
| 12 | | | |

TABLE 1-continued (XV)

| Compound | A | Q | G |
|---|---|---|---|
| 13 | cyclobutyl-O-C(=O)-CH(CH₃)- | 3-(thiophen-2-yl)-2-alkoxy-quinoxalinyl | isopropyl-NH-tetrazolyl |
| 14 | tert-butyl-O-C(=O)-CH(CH₃)- | 3-(styryl)-2-alkoxy-quinoxalinyl | isopropyl-NH-tetrazolyl |
| 15 | tert-butyl-O-C(=O)-CH(CH₃)- | 3-(thiophen-3-yl-vinyl)-2-alkoxy-quinoxalinyl | isopropyl-NH-tetrazolyl |
| 16 | tert-butyl-O-C(=O)-CH(CH₃)- | 3-(2-(thiazol-2-yl)ethyl)-2-alkoxy-quinoxalinyl | isopropyl-NH-tetrazolyl |
| 17 | cyclopentyl-O-C(=O)-CH(CH₃)- | 5,8-dimethoxy-3-(thiophen-2-yl)-2-alkoxy-quinoxalinyl | isopropyl-NH-tetrazolyl |
| 18 | cyclopentyl-O-C(=O)-CH(CH₃)- | 6,7-dichloro-3-(thiophen-2-yl)-2-alkoxy-quinoxalinyl | isopropyl-NH-tetrazolyl |

TABLE 1-continued
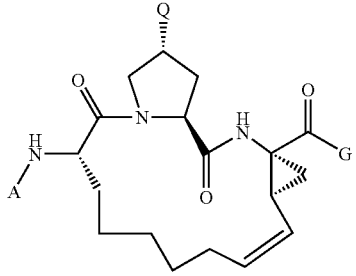
(XV)
| Compound | A | Q | G |
|---|---|---|---|
| 19 | 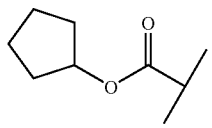 | 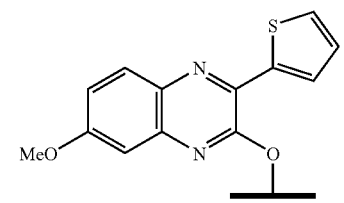 | 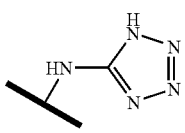 |
| 20 | 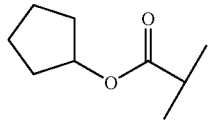 | 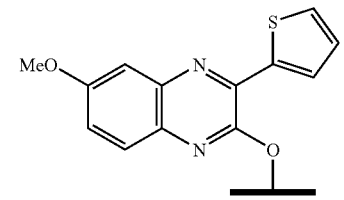 | 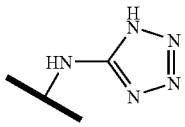 |
| 21 | 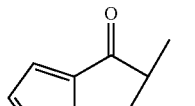 | 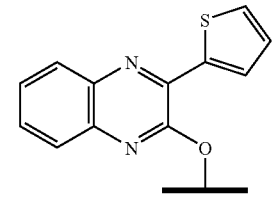 | 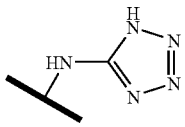 |
| 22 | 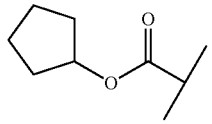 | 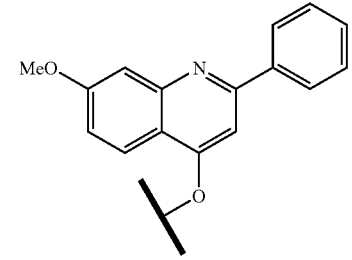 | 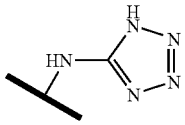 |
| 23 | 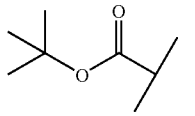 | 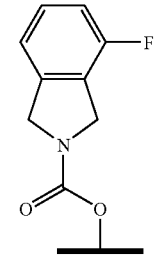 | 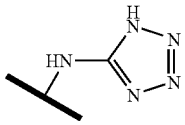 |

TABLE 1-continued (XV)

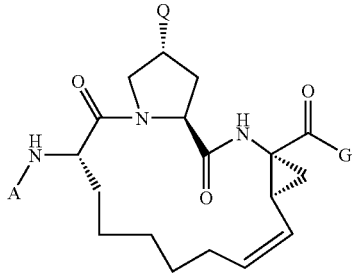

| Compound | A | Q | G |
|---|---|---|---|
| 24 | | 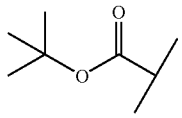 | 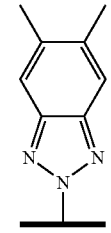 and |
| 25 | | 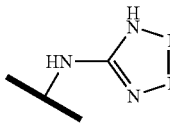 | 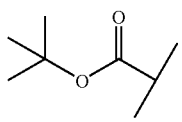. |

9. A pharmaceutical composition comprising therapeutically effective amount of a compound according to claim 1 or a pharmaceutically acceptable salt, or ester thereof, in combination with a pharmaceutically acceptable carrier or excipient.

10. A method of treating a hepatitis C viral infection in a subject, comprising administering to a subject in need thereof a pharmaceutical composition according to claim 9.

11. A method of inhibiting the replication of hepatitis C virus, the method comprising contacting the hepatitis C virus with an inhibitory amount of a compound of claim 1 or a pharmaceutically acceptable salt or ester thereof.

12. A method of claim 10 further comprising administering an additional anti-hepatitis C virus agent.

13. The method of claim 12, wherein said additional anti-hepatitis C virus agent is selected from the group consisting of α-interferon, β-interferon, ribavarin, and adamantine.

14. The method of claim 12, wherein said additional anti-hepatitis C virus agent is an inhibitor of other targets in the hepatitis C virus life cycle which is selected from the group consisting of helicase, polymerase, metalloprotease, and IRES.

15. A compound represented by formula (I):

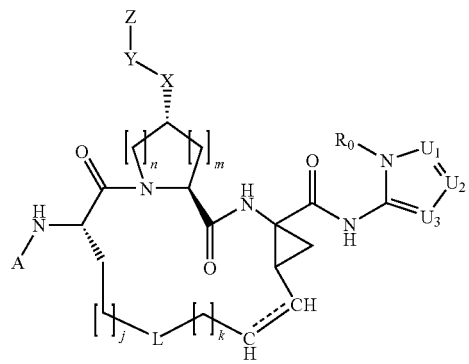

(I)

or a pharmaceutically acceptable salt or ester thereof, wherein:
A is selected from H, —(C═O)—O—$R_1$, —(C═O)—$R_2$, —C(═O)—NH—$R_2$, or —S(O)$_2$—$R_1$, —S(O)$_2$NH$R_2$;
$R_1$ is selected from the group consisting of:
(i) aryl;
(ii) substituted aryl;
(iii) heteroaryl;
(iv) substituted heteroaryl;

(v) heterocycloalkyl or substituted heterocycloalkyl;
(vi) —$C_1$-$C_8$ alkyl;
(vii) —$C_2$-$C_8$ alkenyl;
(viii) —$C_2$-$C_8$ alkynyl containing 0, 1, 2, or 3 heteroatoms selected from O, S and N;
(ix) substituted —$C_1$-$C_8$ alkyl;
(x) substituted —$C_2$-$C_8$ alkenyl;
(xi) substituted —$C_2$-$C_8$ alkynyl containing 0, 1, 2, or 3 heteroatoms selected from O, S and N;
(xii) —$C_3$-$C_{12}$ cycloalkyl;
(xiii) substituted —$C_3$-$C_{12}$ cycloalkyl;
(xiv) —$C_3$-$C_{12}$ cycloalkenyl; and
(xv) substituted —$C_3$-$C_{12}$ cycloalkenyl;
$R_2$ is selected from the group consisting of:
(i) hydrogen;
(ii) aryl;
(iii) substituted aryl;
(iv) heteroaryl;
(v) substituted heteroaryl;
(vi) heterocycloalkyl,
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S and N;
(xi) substituted —$C_1$-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S and N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;
$R_0$ is H, Me, Et, —OH, or —C(O)$NH_2$;
$U_1$, $U_2$, and $U_3$ are independently selected from —$CR_3$ and N, wherein $R_3$ is selected from:
(i) hydrogen;
(ii) halogen;
(iii) —$NO_2$;
(iv) —CN;
(v) -M-$R_4$, wherein M is absent, O, S, NH, or $NR_5$;
(vi) aryl;
(vii) substituted aryl;
(viii) heteroaryl;
(ix) substituted heteroaryl;
(x) heterocycloalkyl; and
(xi) substituted heterocycloalkyl;
each $R_4$, $R_5$ is independently selected from:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl;
(ix) —$C_2$-$C_8$ alkenyl;
(x) —$C_2$-$C_8$ alkynyl containing 0, 1, 2, or 3 heteroatoms selected from O, S and N;
(xi) substituted —Chd 1-$C_8$ alkyl;
(xii) substituted —$C_2$-$C_8$ alkenyl;
(xiii) substituted —$C_2$-$C_8$ alkynyl containing 0, 1, 2, or 3 heteroatoms selected from O, S and N;
(xiv) —$C_3$-$C_{12}$ cycloalkyl;
(xv) substituted —$C_3$-$C_{12}$ cycloalkyl;
(xvi) —$C_3$-$C_{12}$ cycloalkenyl; and
(xvii) substituted —$C_3$-$C_{12}$ cycloalkenyl;
L is selected from —$CH_2$—, —O—, —S—, —$S(O)_2$—, —CO—, —C(O)O—, —C(O)NH—, —CHF—, —$CF_2$—, aryl, substituted aryl, heteroaryl and substituted heteroaryl;
X is absent or is selected from the group consisting of:
(i) oxygen;
(ii) sulfur; and
(iii) $NR_4$;
Y is absent or is selected from the group consisting of:
(i) —$C_1$-$C_6$ alkyl containing 0, 1, 2, or 3 heteroatoms selected from O, S and N, optionally substituted with one or more substituent selected from halogen, aryl, substituted aryl, heteroaryl, and substituted heteroaryl;
(ii) —$C_2$-$C_6$ alkenyl containing 0, 1, 2, or 3 heteroatoms selected from O, S and N, optionally substituted with one or more substituent selected from halogen, aryl, substituted aryl, heteroaryl, and substituted heteroaryl;
(iii) —$C_2$-$C_6$ alkynyl containing 0, 1, 2, or 3 heteroatoms selected from O, S and N, optionally substituted with one or more substituent selected from halogen, aryl, substituted aryl, heteroaryl, and substituted heteroaryl;
(iv) —$C_3$-$C_{12}$ cycloalkyl;
(v) substituted —$C_3C_{12}$ cycloalkyl;
(vi) heterocycloalkyl; and
(vii) substituted heterocycloalkyl;
Z is selected from aryl, substituted aryl, heteroaryl, and substituted heteroaryl;
j=0, 1, 2, 3, or 4;
k=1, 2, or 3;
m=0, 1, or 2;
n=1, or 2; and
----- denotes a carbon-carbon single or double bond.

* * * * *

UNITED STATES PATENT AND TRADEMARK OFFICE
CERTIFICATE OF CORRECTION

| | | |
|---|---|---|
| PATENT NO. | : 7,605,126 B2 | Page 1 of 1 |
| APPLICATION NO. | : 11/503502 | |
| DATED | : October 20, 2009 | |
| INVENTOR(S) | : Niu et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 185 days Delete the phrase "by 185 days" and insert -- by 195 days --

Signed and Sealed this

Fourth Day of May, 2010

David J. Kappos
*Director of the United States Patent and Trademark Office*